(12) United States Patent
Yu et al.

(10) Patent No.: US 9,582,940 B2
(45) Date of Patent: Feb. 28, 2017

(54) SYSTEM AND METHOD FOR IMAGE COMPOSITION

(71) Applicant: SHANGHAI UNITED IMAGING HEALTHCARE CO., LTD., Shanghai (CN)

(72) Inventors: Wenjun Yu, Shanghai (CN); Xiangcui Jin, Shanghai (CN); Yang Hu, Shanghai (CN); Haifeng Xiao, Shanghai (CN); Hongwei Chen, Shanghai (CN); Wei Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 15/081,892

(22) Filed: Mar. 27, 2016

(65) Prior Publication Data
US 2016/0247325 A1  Aug. 25, 2016

Related U.S. Application Data

(63) Continuation of application No. PCT/CN2015/090265, filed on Sep. 22, 2015.

(30) Foreign Application Priority Data

Sep. 22, 2014 (CN) .......................... 2014 1 0487252
Sep. 28, 2014 (CN) .......................... 2014 1 0508290

(51) Int. Cl.
*G06K 9/00* (2006.01)
*G06T 19/20* (2011.01)
(Continued)

(52) U.S. Cl.
CPC ............ *G06T 19/20* (2013.01); *A61B 6/4452* (2013.01); *A61B 6/4476* (2013.01); *A61B 6/504* (2013.01);
(Continued)

(58) Field of Classification Search
CPC ..... A61B 6/4452; A61B 6/4476; A61B 6/504; A61B 6/5241; A61B 6/4464; A61B 6/467;
(Continued)

(56) References Cited

U.S. PATENT DOCUMENTS 6,097,833 A  8/2000 Lobregt et al.
6,714,668 B1 * 3/2004 Kerrien ................. G06T 3/0006
382/130
(Continued)

FOREIGN PATENT DOCUMENTS

CN  101756707 A  6/2010
CN  102138803 A  8/2011
(Continued)

OTHER PUBLICATIONS

International Search Report for PCT/CN2015/090265 mailed on Jan. 12, 2016, 5 pages.
(Continued)

*Primary Examiner* — Mekonen Bekele
(74) *Attorney, Agent, or Firm* — Metis IP LLC

(57) ABSTRACT

A system and method for obtaining a composite image by combining multiple sub-images are provided. In some embodiments, the method may include retrieving overlapping images corresponding to sub-images including 3D volume data, generating two-dimensional (2D) projection images and pixel maps based on the overlapping images, performing one or more registrations based on the 2D projection images and the pixel maps, calibrating the sub-images based on the results of the registration(s), and fusing the sub-images to produce a composite image. In some embodiments, the method may include setting a plurality of parameters relating to an X-radiation source or a radiation detector based on a preliminary number of exposures and a
(Continued)

preliminary exposure region, controlling, based on at least one of the plurality of parameters, a motion of the X-radiation source or a motion of the radiation detector to capture a plurality of sub-images, and combining the plurality of sub-images.

11 Claims, 34 Drawing Sheets

(51) Int. Cl.
    *G06T 5/50*           (2006.01)
    *G06T 7/00*           (2006.01)
    *A61B 6/00*           (2006.01)
    *G06F 19/00*          (2011.01)

(52) U.S. Cl.
    CPC .......... *A61B 6/5241* (2013.01); *G06F 19/321* (2013.01); *G06T 5/50* (2013.01); *G06T 7/0024* (2013.01); *G06T 7/0026* (2013.01); *A61B 6/4464* (2013.01); *A61B 6/467* (2013.01); *G06T 2207/10081* (2013.01); *G06T 2207/10088* (2013.01); *G06T 2207/10104* (2013.01); *G06T 2207/10108* (2013.01); *G06T 2207/10116* (2013.01); *G06T 2207/10132* (2013.01); *G06T 2207/10136* (2013.01); *G06T 2207/20221* (2013.01); *G06T 2211/404* (2013.01)

(58) Field of Classification Search
    CPC ......... G06F 19/321; G06T 19/20; G06T 5/50; G06T 7/0024; G06T 7/0026; G06T 2207/10088; G06T 2207/10104; G06T 2207/10108; G06T 2207/10081
    USPC .......................................... 382/130, 128, 154
    See application file for complete search history.

(56) References Cited

U.S. PATENT DOCUMENTS

| | | | |
|---|---|---|---|
| 6,879,711 B2* | 4/2005 | Maurincomme | G06T 5/50 128/922 |
| 7,423,428 B2 | 9/2008 | Kuhara | |
| 7,430,312 B2* | 9/2008 | Gu | G01B 11/25 345/419 |
| 7,522,701 B2 | 4/2009 | Jensen et al. | |
| 7,555,100 B2 | 6/2009 | Wang et al. | |
| 8,360,639 B2 | 1/2013 | Kato | |
| 9,020,218 B2* | 4/2015 | Hakl | G06T 15/08 382/128 |
| 9,135,706 B2 | 9/2015 | Zagorchev et al. | |
| 2001/0034439 A1* | 10/2001 | Villeponteau | A61L 29/14 536/24.5 |
| 2004/0247081 A1 | 12/2004 | Halsmer et al. | |
| 2006/0052686 A1 | 3/2006 | Zhang et al. | |
| 2006/0210146 A1* | 9/2006 | Gu | G01B 11/25 382/154 |
| 2008/0118143 A1* | 5/2008 | Gordon | G01B 11/2513 382/154 |
| 2008/0199071 A1* | 8/2008 | Gu | G01B 11/25 382/154 |
| 2010/0034439 A1* | 2/2010 | Asano | G06T 7/0083 382/128 |
| 2010/0067762 A1 | 3/2010 | Glocker et al. | |
| 2010/0119129 A1* | 5/2010 | Moriya | G06T 7/0081 382/128 |
| 2010/0150418 A1* | 6/2010 | Moriya | G06T 19/00 382/128 |
| 2011/0188726 A1 | 8/2011 | Nathaniel et al. | |
| 2014/0267267 A1 | 9/2014 | Piper | |
| 2016/0206268 A1* | 7/2016 | Fukuda | A61B 6/025 |

FOREIGN PATENT DOCUMENTS

| | | |
|---|---|---|
| CN | 102316806 A | 1/2012 |
| CN | 103150715 A | 6/2013 |
| CN | 203424940 U | 2/2014 |
| CN | 103871036 A | 6/2014 |
| CN | 104268846 A | 1/2015 |
| CN | 104287756 A | 1/2015 |
| EP | 0861556 B1 | 2/1998 |

OTHER PUBLICATIONS

English translation of Office Action in corresponding Chinese Application No. 201410508290.0 mailed Jan. 26, 2016, 5 pages.

\* cited by examiner

SYSTEM AND METHOD FOR IMAGE COMPOSITION

CROSS-REFERENCE TO RELATED APPLICATIONS

This application is a continuation of International Application No. PCT/CN2015/090265 filed on Sep. 22, 2015, designating the United States of America, which in turn claims priority of Chinese Application No. 201410487252.1 filed on Sep. 22, 2014, and Chinese Application No. 201410508290.0 filed on Sep. 28, 2014, the entire contents of each of which are hereby incorporated by reference.

TECHNICAL FIELD

The present disclosure generally relates to image processing, and more particularly, to a system and method for combining sub-images into a composite image.

BACKGROUND

Medical imaging techniques, such as X-ray, magnetic resonance imaging (MM), computed tomography (CT), are widely used for disease diagnosis. A region of interest, such as one or more blood vessels in a limb, a spinal column, or a portion thereof, may be visualized using one or more of the techniques mentioned above.

However, when performing an imaging operation on a region of interest whose size is larger than the field of view (FOV) of an imaging device (for example, a CT scanner, an X-ray scanner, an MM scanner, a MicroCT scanner), a single imaging operation may be inadequate to obtain an image of the entire region of interest; merely a portion of the region of interest may be included in an image. Under such a circumstance, multiple imaging operations may need to be performed on the region of interest to generate a series of sub-images and a sub-image covers only a portion of the region of interest. By combining the sub-images, a composite image covering the entire region of interest may be generated.

Meanwhile, in an imaging operation using a radiation-based imaging technique, such as X-ray, CT, radiation damage may occur due to extended exposure of a region of interest (for example, a human body or a portion thereof) to radiation. Thus, it may be desirable to develop a method and system that may reduce the radiation dose applied to a human patient and perform an imaging composition on multiple successive sub-images of a region of interest.

SUMMARY

In a first aspect of the present disclosure, an image composition system is provided. In some embodiments, the image composition system may include a parameter setting engine, an acquisition engine, an image processing engine, and a storage engine. The parameter setting engine may be configured to set one or more parameters relating to, for example, image acquisition, image processing, or the like, or any combination thereof. The acquisition engine may be configured to retrieve a first sub-image and a second sub-image, the first sub-image and the second sub-image may correspond to three-dimensional (3D) volume data. The image processing engine may be configured to retrieve a first overlapping image from the first sub-image, retrieve a second overlapping image from the second sub-image, generate a first two-dimensional (2D) projection image and a first pixel map based on maximum intensity projection of the first overlapping image onto a plane, generate a second 2D projection image and a second pixel map based on maximum intensity projection of the second overlapping image onto the plane, perform 2D registration based on the first 2D projection image, the first pixel map, the second 2D projection image, and the second pixel map, perform 3D registration based on the 2D registration, the first pixel map and the second pixel map, identify a correlation between the first sub-image and the second sub-image based on the 2D registration or the 3D registration, and fuse the first overlapping image and the second overlapping image based on the correlation to provide a composite image.

In a second aspect of the present disclosure, a method is provided. The method may include one or more of the following operations. A first sub-image and a second sub-image may be retrieved. Both the first sub-image and the second sub-image may correspond to 3D volume data. A first overlapping image may be retrieved from the first sub-image, and a second overlapping image may be retrieved from the second sub-image. A first 2D projection image and first pixel map may be generated based on maximum intensity projection of the first overlapping image onto a plane. A second 2D projection image and second pixel map may be generated based on maximum intensity projection of the second overlapping image onto the plane. Two-dimensional registration may be performed based on the first 2D projection image, the first map, the second 2D projection image, and the second pixel map. Three-dimensional registration may be performed based on the 2D registration, the first pixel, and the second pixel map. A correlation between the first sub-image and the second sub-image may be identified based on the 2D registration or the 3D registration. The first overlapping image and the second overlapping image may be fused based on the correlation to provide a composite image.

In some embodiments, the first sub-image or the second sub-image may be, for example, a 3D image, a 2D image, or the like, or a combination thereof. The 3D images may be 3D-DSA images. Optionally and preferably, the 3D-DSA images may be 3D digital coronal images, 3D digital sagittal images, 3D digital transverse images, or the like, or a combination thereof.

In the embodiments, the plane may include a coronal plane, a sagittal plane, or a transverse plane.

In some embodiments, the first sub-image or the second sub-image may be retrieved by using DSA (digital subtraction angiography), CT (computed tomography), CTA (computed tomography angiography), PET (positron emission tomography), X-ray, MRI (magnetic resonance imaging), MRA (magnetic resonance angiography), SPECT (single-photon emission computerized tomography), US (ultrasound scanning).

In some embodiments, the first overlapping image and the second overlapping image may be retrieved by using Digital Imaging and Communication in Medicine (DICOM). Specifically, label (0020 0032) of DICOM may be used to retrieve the first overlapping image and the second overlapping image.

In some embodiments, an offset may be generated by performing 2D registration, the offset may include, for example, an X offset, a Y offset, a Z offset, a coronal offset, a sagittal offset, or a transverse offset.

In some embodiments, another offset may be generated by performing 3D registration. The offset may be in the direction perpendicular to the plane onto which the overlapping images have been projected to generate the 2D projection images. The offset may include, for example, an X offset, a Y offset, a Z offset, a coronal offset, a sagittal offset, a transverse offset.

In some embodiments, a fine registration may be performed based on the 2D registration and/or the 3D registration discussed elsewhere. The fine registration may be based on an algorithm including, for example, recursion, a bisection method, an exhaustive method, a greedy algorithm, a divide and conquer algorithm, dynamic programming method, an iterative method, a branch-and-bound algorithm, a backtracking algorithm, or the like, or a combination thereof.

In some embodiments, the second pixel map may include a calibrated pixel map based on the 2D registration. Specifically, the second pixel map may be calibrated based on the 2D offsets to generate the calibrated pixel map. In some embodiments, one of the first pixel map and the second pixel map may be a reference pixel map, and the other pixel map may be a floating pixel map.

In some embodiments, the first pixel map may include information identifying the location of maximum intensity of the first overlapping image, and the location may be in a direction perpendicular to a plane onto which the first overlapping image is projected. In some embodiments, the second pixel map may include information identifying the location of maximum intensity of the second overlapping image, and the location may be in a direction perpendicular to the same plane.

In some embodiments, the 3D registration may include calculating a plurality of differences in the locations in the direction perpendicular to the plane between the first pixel map and the second pixel map, each one of the plurality of differences corresponding to a pixel within the plane, comparing the plurality of differences to obtain a probability of the differences and designating an offset in the direction perpendicular to the plane based on the probability.

In a third aspect of the present disclosure, another image composition system is provided. The image composition system may include an imaging device and a processor. The imaging device may include an X-radiation source and a radiation detector. The processor may include a parameter setting engine, a control engine and an image processing engine. The parameter setting engine may be configured to set a plurality of parameters relating to the X-radiation source or the radiation detector based on one or more preliminary parameters. The control engine may be configured to control a motion of the X-radiation source or a motion of the radiation detector to capture a plurality of sub-images. The image processing engine may be configured to combine the plurality of sub-images.

In a fourth aspect of the present disclosure, another method for image composition is provided. The method may include: setting a plurality of parameters relating to the X-radiation source or the radiation detector based on one or more preliminary parameters; controlling, based on at least one of the plurality of parameters, a motion of the X-radiation source or a motion of the radiation detector to capture a plurality of sub-images; combining the plurality of sub-images.

In some embodiments, the preliminary parameters may include at least one of a dimension of an exposure region, a number of exposures, an overlapping region between two adjacent exposures, a starting position of an effective light field, an ending position of the effective light field, or a height of the effective light field.

In some embodiments, a plurality of secondary parameters may be obtained based on one or more preliminary parameters. The secondary parameters may include at least one of a dimension of an exposure region, a number of exposures, an overlapping region between two adjacent exposures, a starting position of an effective light field, an ending position of the effective light field, or a height of the effective light field.

In some embodiments, the difference between the secondary number of exposure and the preliminary number of exposure may be less than 1. In some embodiments, the secondary exposure region may be equal to or smaller than the preliminary exposure region.

In some embodiments, the imaging device may be configured according to at least one or more of the preliminary parameters. In some embodiments, the imaging device may be configured according to at least one or more of the secondary parameters.

In some embodiments, the X-radiation source may include a tube configured to generate a beam of one or more X-rays, and a beam limiting device mounted proximal to the X-radiation source. The beam limiting device may function to define the beam of one or more X-rays generated by the tube. In some embodiments, the height of the effective light field may equal to a product of the opening of the beam limiting device in the vertical direction and a constant k. In some embodiments, the secondary height of the effective light field may be equal to or smaller than the preliminary height of the effective light field. In some embodiments, the tube, the beam limiting device, and the radiation detector may be positioned according to the preliminary parameters at an exposure. In some embodiments, the tube, the beam limiting device, and the radiation detector may be positioned according to the secondary parameters at an exposure.

In some embodiments, the tube (or an X-radiation source) and the radiation detector may move simultaneously and/or in a synchronized fashion. In some embodiments, the tube (or an X-radiation source) and the radiation detector may move one after another.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "engine," "unit," "module," and/or "block" used herein are one method to distinguish different components, elements, parts, section or assembly of different level in ascending order. However, the terms may be displaced by other expression if they may achieve the same purpose.

It will be understood that when a unit, engine, module or block is referred to as being "on," "connected to" or "coupled to" another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an" and "the" may be intended to include the plural forms as well, unless the context clearly indicates otherwise. It will be further understood that the terms "include," and/or "comprising," when used in this disclosure, specify the presence of integers, devices, behaviors, stated features, steps, elements, operations, and/or components, but do not exclude the presence or addition of one or more other integers, devices, behaviors, features, steps, elements, operations, components, and/or groups thereof.

Figure 1:
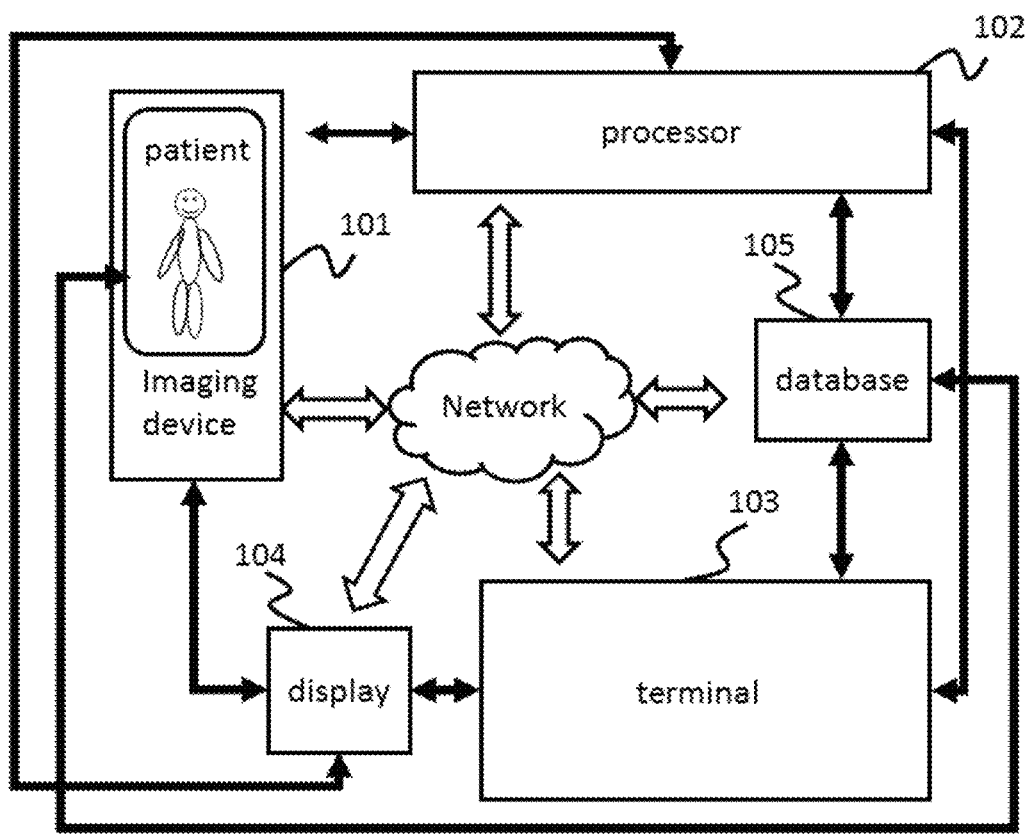
FIG. 1 is a block diagram depicting an image composition system according to some embodiments of the present disclosure.

FIG. 1 illustrates a block diagram of an image composition system 100 according to some embodiments of the present disclosure. The image composition system 100 may include an imaging device 101, a processor 102, a terminal 103, a display 104, and a database 105. The imaging device 101 may be configured to generate or provide one or more images of a region of interest. Merely by way of example, the imaging device 101 may include an X-radiation source and a radiation detector.

The images may be three-dimensional (3D) images, two-dimensional (2D) images, or the like, or a combination thereof. For instance, the 3D images may be three-dimensional digital subtraction angiography images (3D-DSA images). Specifically, the 3D-DSA images may be 3D digital coronal images, 3D digital sagittal images, 3D digital transverse images, or the like, or a combination thereof. As used herein, an overlapping image may depict an overlapping region of a number of sub-images regardless of whether they are successive or not. For instance, an overlapping image may depict an overlapping region of two successive sub-images. In some embodiments, each of the sub-images may include an overlapping image. An overlapping image may be part of a sub-image. As used herein, a sub-image may refer to an image of a portion of a region of interest. A set of 3D volume data may correspond to a stack of 2D images. In some embodiments, a 2D image may be referred to as a slice. For instance, a set of 3D volume data may correspond to a stack of 2D images in the coronal plane. As used herein, such a stack of 2D images may be referred to as a 3D coronal image. A same set of 3D volume data may correspond to different stacks of 2D images in different planes. For instance, a same set of 3D volume data may correspond to a stack of 2D images in the coronal plane, and also a stack of 2D images in the transverse plane. Descriptions regarding a coronal plane and a transverse plane may be found elsewhere in the present disclosure. See, for example, FIG. 7 and the description thereof. The overlapping region corresponding to a set of 3D volume data may be depicted by a stack of 2D overlapping images.

The image device 101 may utilize a technique including, for example, digital subtraction angiography (DSA), computed tomography (CT), computed tomography angiography (CTA), positron emission tomography (PET), X-ray, digital radiation (DR), magnetic resonance imaging (MM), magnetic resonance angiography (MRA), single-photon emission computerized tomography (SPECT), ultrasound scanning (US), or the like, or a combination thereof.

The processor 102 may be configured to process the images acquired by the imaging device 101 or retrieved from another source (for example, an imaging device, a database or storage, or the like, or a combination thereof). The processor 102 may include a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an acorn reduced instruction set computing (RISC) machine (ARM), or the like, or any combination thereof. The processor 102 may generate a control signal relating to the configuration of the imaging device 101.

The terminal 103 may communicate with the processor 102 and allow one or more operators to control the production and/or display of images on the display 104. The terminal 103 may include an input device, a control panel (not shown in the figure), etc. The input device may be a keyboard, a touch screen, a mouse, a remote controller, or the like, or any combination thereof. An input device may include alphanumeric and other keys that may be inputted via a keyboard, a touch screen (for example, with haptics or tactile feedback), a speech input, an eye tracking input, a brain monitoring system, or any other comparable input mechanism. The input information received through the input device may be communicated to the processor 102 via, for example, a bus, for further processing. Another type of the input device may include a cursor control device, such as a mouse, a trackball, or cursor direction keys to communicate direction information and command selections to, for example, the processor 102 and to control cursor movement on the display 104 or another display device.

The display 104 may be configured to display information. Exemplary information may include, for example, an image before and/or after image processing, a request for input or parameter relating to image acquisition and/or processing, or the like, or a combination thereof. The display device may include a liquid crystal display (LCD), a light emitting diode (LED)-based display, a flat panel display or curved screen (or television), a cathode ray tube (CRT), or the like, or a combination thereof.

The database 105 may be configured to store images and/or relevant information or parameters. Exemplary parameters may include an exposure region, the number of exposures, the overlapping region between two adjacent (or successive) exposures, the starting position of the effective light field, the ending position of the effective light field, the height of the effective light field, or the like, or a combination thereof.

It should be noted that the flowchart described above is provided for the purposes of illustration, and not intended to limit the scope of the present disclosure. For persons having ordinary skills in the art, various variations and modifications may be conducted under the guidance of the present disclosure. However, those variations and modifications do not depart the scope of the present disclosure. For example, the imaging device 101, the processor 102, the terminal 103, the display 104, and the database 105 may communicate with each other via a network.

Figure 2:
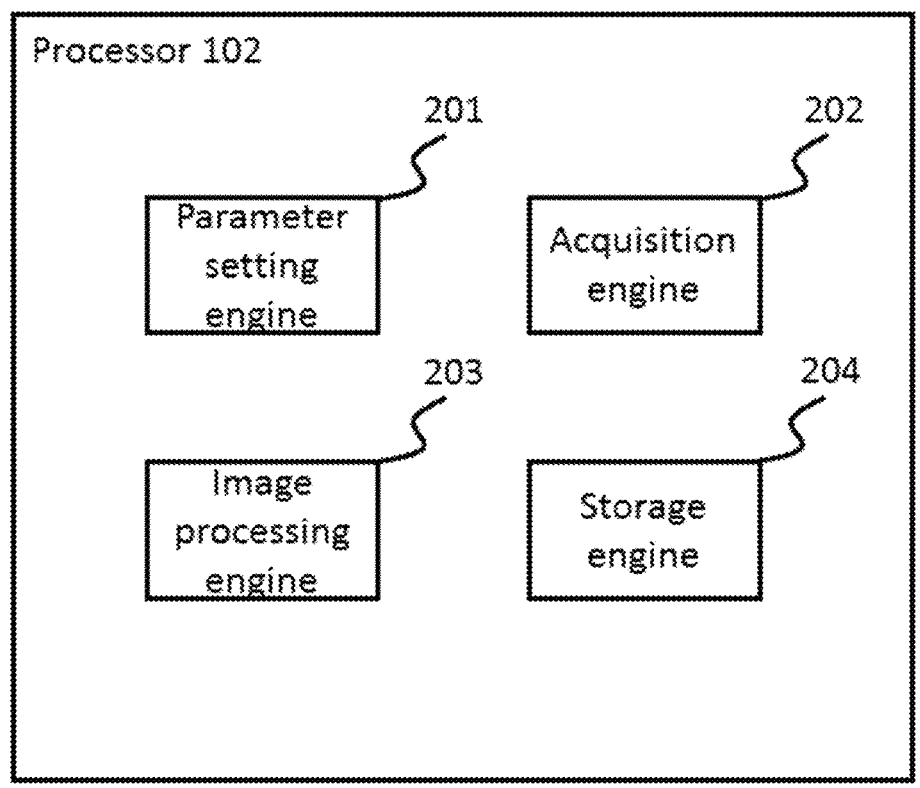
FIG. 2 is a block diagram depicting a processor according to some embodiments of the present disclosure.

FIG. 2 is a block diagram of the processor 102 according to some embodiments of the present disclosure. The processor 102 may include a parameter setting engine 201, an acquisition engine 202, an image processing engine 203, and a storage engine 204. The parameter setting engine 201 may be configured to set one or more parameters relating to, for example, image acquisition, image processing, or the like, or a combination thereof. Exemplary parameters may include an exposure region, the number of exposures, the overlapping region between two adjacent exposures, the starting position of the effective light field, the ending position of the effective light field, the height of the effective light field, or the like, or a combination thereof. The processor 102 may include a control engine (not shown in the figure). The control engine may control one or more components of the image composition system 100 based on one or more parameters provided by the parameter setting engine 201. Merely by way of example, the control engine may control the motion of one or more components of the imaging device 101 including the X-radiation source and/or the radiation detector.

The acquisition engine 202 may be configured to acquire one or more images. The image(s) may be obtained by the imaging device 101 or retrieved from another source (for example, an imaging device, a database or storage, or the like, or a combination thereof). Exemplary images may include a composite image, sub-images of a region of interest (acquired through, for example, a series of scans of a region of interest), overlapping images of the sub-images, or the like, or a combination thereof. As used herein, a composite image may refer to an image of an entire region of interest. In some embodiments, a composite image may be constructed by way of combining a plurality of sub-images. In some embodiments, the combination may be achieved by fusing the overlapping images of two sub-images, for example, two adjacent sub-images. Two sub-images may be considered adjacent or successive if they depict adjoining portions of a region of interest.

The image processing engine 203 may be configured to process images acquired by the acquisition engine 202. The processing may include, for example, calculating the number of exposures, performing registration of images (for example, registration of overlapping images), fusing overlapping images, combining sub-images, or the like, or a combination thereof. The registration may include 2D registration, 3D registration, or the like, or a combination thereof. The storage engine 204 may be configured to storage images and/or relevant information or parameters.

Figure 3:
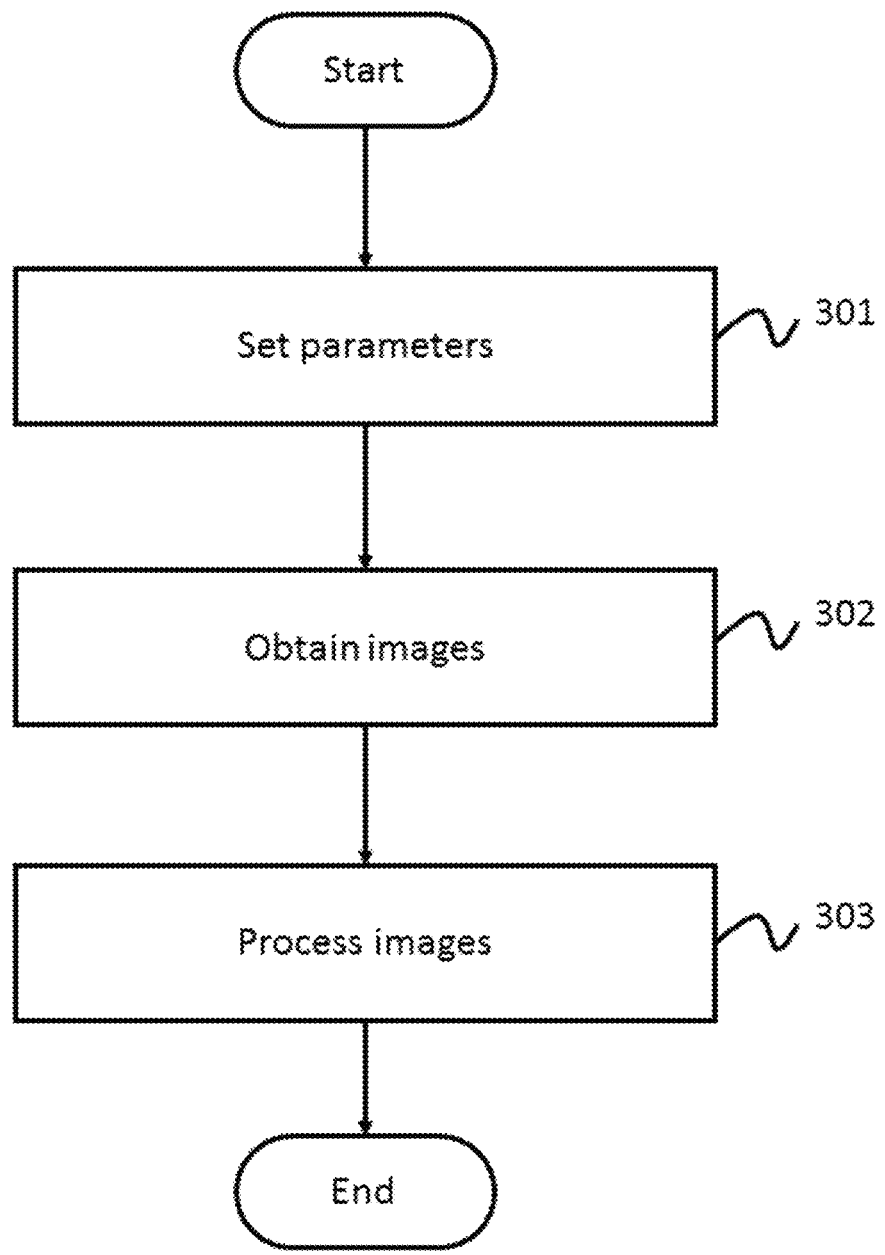
FIG. 3 is a flowchart illustrating a workflow for image processing according to some embodiments of the present disclosure.

FIG. 3 is a flowchart illustrating a process of image processing according to some embodiments of the present disclosure. In step 301, one or more parameters may be set. Exemplary parameters may include an exposure region, the number of exposures, the overlapping region between two adjacent exposures, the starting position of the effective light field, the ending position of the effective light field, the height of the effective light field, or the like, or a combination thereof. In step 302, one or more images may be obtained. The images may include a composite image, sub-images of a region of interest (acquired through, for example, a series of scans of the region of interest), overlapping images of the sub-images, or the like, or a combination thereof. The images obtained in step 302 may be processed in step 303. Exemplary processing may include calculating the number of exposures, performing registration of images (for example, overlapping images), fusing the overlapping images of sub-images to generate a composite image, or the like, or a combination thereof. The registration may include 2D registration, 3D registration, or the like, or a combination thereof.

It should be noted that the flowchart described above is provided for the purposes of illustration, and may not intend to limit the scope of the present disclosure. For persons having ordinary skills in the art, various variations and modifications may be conducted under the guidance of the present disclosure. However, those variations and modifications do not depart the scope of the present disclosure.

In some embodiments, a composite image may be generated by way of combining a plurality of sub-images. The sub-images may be acquired using an imaging device or an imaging system according to one or more parameters. To obtain a composite image and/or the corresponding sub-images, at least some of the parameters relating to the configuration of the imaging device or imaging system may be adjusted for individual patients. Merely by way of example, to obtain an X-ray image of an entire spinal column of a patient, a user or operator (for example, a healthcare provider, an imaging specialist, etc.) may designate or adjust parameters including, for example, an exposure region, the overlapping region between adjacent exposures, the number of exposures, or the like, or a combination thereof. As another example, a composite image of blood vessels in a lower limb of a patient may be obtained by way of image processing. An exemplary image processing procedure may include acquiring a plurality of DSA sub-images of the blood vessels of the lower limb, performing 2D registration and/or 3D registration of overlapping images of adjacent DSA sub-images, fusing overlapping images based on the 2D registration and/or 3D registration to combine the DSA sub-images. As a further example, a composite image may be obtained by adjusting one or more parameters relating to the configuration of an imaging device or imaging system, acquiring a plurality of sub-images, and processing the acquired sub-images based on 2D registration and/or 3D registration of overlapping images of sub-images. It should be noted that the examples described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure.

Figure 4:
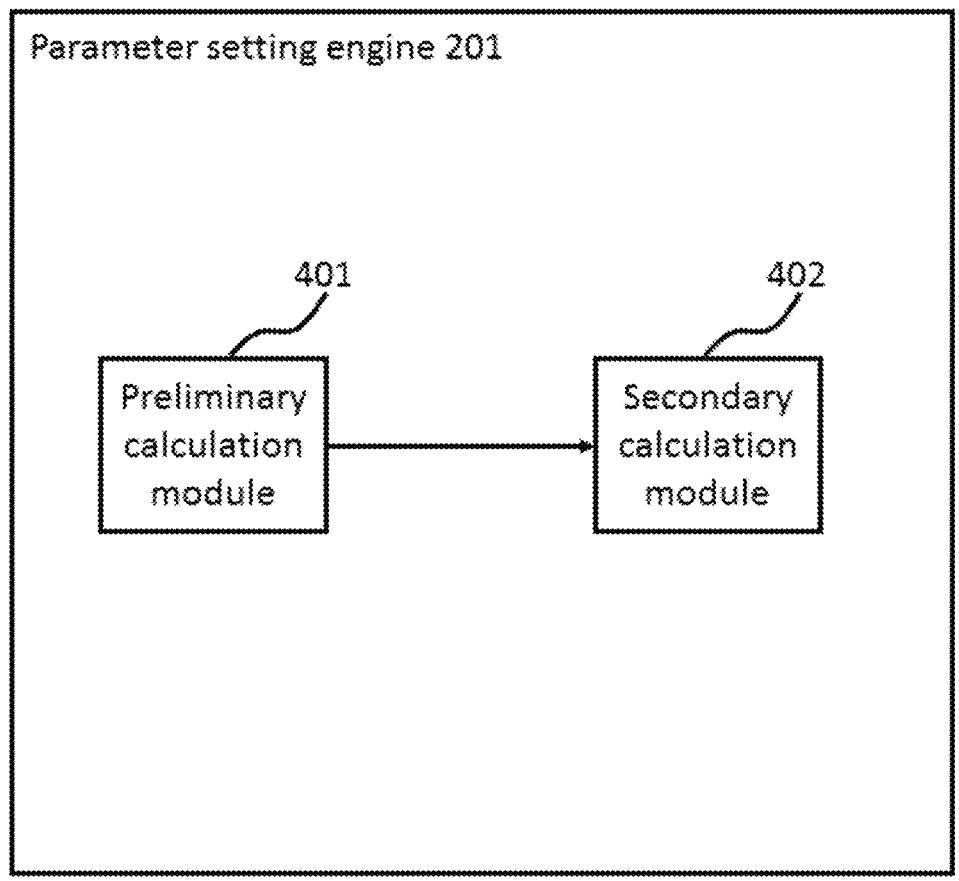
FIG. 4 is a block diagram illustrating an architecture of a parameter setting engine according to some embodiments of the present disclosure.

FIG. 4 is a block diagram illustrating an architecture of a parameter setting engine 201 according to some embodiments of the present disclosure where a composite image may be acquired by adjusting the parameters relating to the configuration of an imaging device or an imaging system. The parameter setting engine 201 may be connected to or otherwise communicate with, for example, the acquisition engine 202, the image processing engine 203, and the storage engine 204. In some embodiments, the parameter setting engine 201 may be connected to or communicate with the imaging device 101, the display 104, the terminal 103, the database 105, or the like, or a combination thereof. At least some of the connection or communication may be achieved via a wired connection, or wirelessly.

The parameter setting engine 201 may be configured to set or adjust one or more parameters relating to the configuration of the imaging device or the imaging system. The parameter setting engine 201 may include a preliminary calculation module 401 and a secondary calculation module 402. In some embodiments, the parameter setting engine 201 may further include an acquisition module (not shown in the figure) configured to acquire information at least part of which may be used by another component of the parameter setting engine 201 or the image composition system 100. In some embodiments, the parameter setting engine 201 may further include a storage module (not shown in the figure) configured to store the parameters calculated by the preliminary calculation module 401 or used in the calculation, and the secondary calculation module 402.

The above description regarding the parameter setting engine 201 are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

The preliminary calculation module 401 may be configured to estimate or calculate one or more preliminary parameters. In some embodiments, the preliminary parameters may be used to configure the imaging device 101. For example, in some embodiments where an X-ray examination is desired, a non-exclusive list of preliminary parameters may include: an exposure region, the number of exposures, the overlapping region between two adjacent exposures, the starting position of the effective light field, the stopping position of the effective light field, the height of the effective light field, etc. The effective light field may refer to the light field received by the detector that may be effective to generate image data. The height of the effective light field may correlate to the opening of a beam limiting device in the length direction (for example, along the direction from the head to the feet of a patient, or vice versa) between a starting position and a stopping position. Merely by way of example, a patient subject to an imaging operation is in a standing position, the starting position of the effective light field may refer to the upper edge of the effective light field corresponding to the first exposure of a number of exposures; the stopping position of the effective light field may refer to the lower edge of the effective light field corresponding to the last exposure of a number of exposures. The above description regarding the preliminary parameters are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

One or more preliminary parameters may be calculated using the preliminary calculation module 401. In some embodiments of the present disclosure, the preliminary parameters may be calculated based on the initial parameters provided by the image composition system 100 during initialization. In some embodiments, a non-exclusive list of initial parameters that may be provided by the image composition system 100 during initialization may include: an exposure region, the number of exposures, the overlapping region between two adjacent exposures, the starting position of the effective light field, the stopping position of the effective light field, the height of the effective light field, etc. In some embodiments of the present disclosure, the initial parameters may be stored in the imaging device 101 or the storage engine 204. In some embodiments of the present disclosure, one or more preliminary parameters may be provided by a user. For example, in some embodiments where an X-ray examination is desired, the image composition system 100 may allow a user to designate a preliminary exposure region. The preliminary exposure region may refer to the entire exposure region that a user may desire to image with respect to a target body (for example, a patient or a portion thereof). In some embodiments of the present disclosure, preliminary parameters may be calculated based on at least some of the user input or designation. For example, in some embodiments where an X-ray examination is desired, a preliminary number of exposures may be calculated based on the preliminary exposure region designated by the user.

The secondary calculation module 402 may be configured to estimate or calculate a secondary parameter according to at least some of the preliminary parameters calculated by the preliminary calculation module 401. In some embodiments, the secondary parameter may be used to configure the imaging device 101. For example, in some embodiments where an X-ray examination is desired, a non-exclusive list of secondary parameters may include: an exposure region, the number of exposures, the overlapping region between two adjacent exposures, the starting position of the effective light field, the stopping position of the effective light field, the height of the effective light field, etc. In some embodiments of the present disclosure, the secondary parameters may include the same parameters as those included in the preliminary parameters. In some embodiments, a secondary parameter may be calculated based on the preliminary parameters from the preliminary calculation module 401. The calculation of a secondary parameter may be performed based on a rule. Merely by way of example, in some embodiments where an X-ray examination is desired, the rule may be that the number of exposures is an integer. In some embodiments where the preliminary number of exposures calculated by the preliminary calculation module 401 is not an integer, the preliminary number of exposures may be adjusted to provide a secondary number of exposures that is an integer. For instance, the preliminary number of exposures may be rounded to the preceding integer or the next integer, and other preliminary parameters may be adjusted accordingly to obtain one or more secondary parameters.

Figure 5:
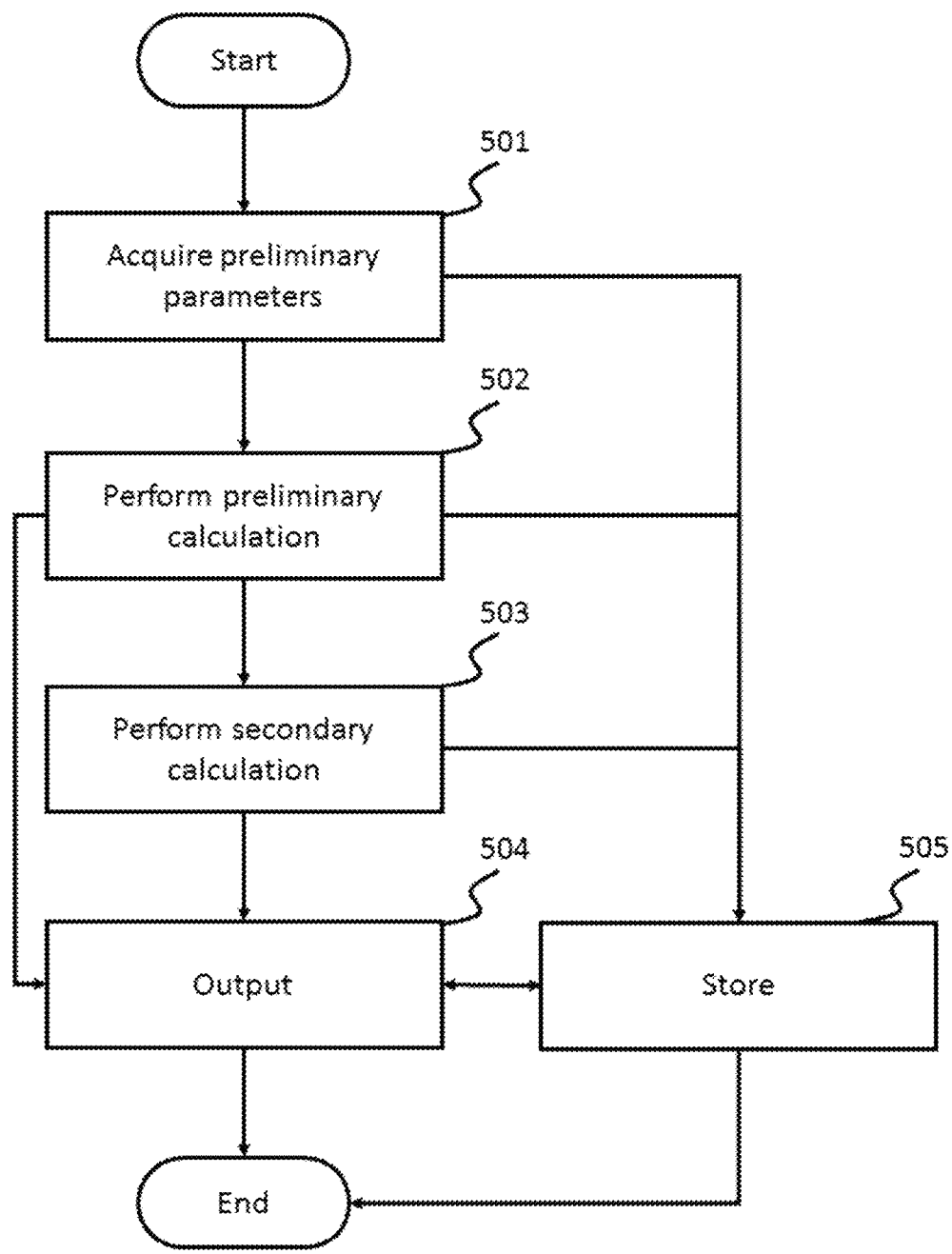
FIG. 5 is a flowchart of an exemplary process for setting parameters according to some embodiments of the present disclosure.

FIG. 5 is a flowchart illustrating an exemplary process for setting parameters according to some embodiments of the present disclosure. It should be noted that the flowchart described below is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure.

Beginning in step 501, one or more preliminary parameters may be acquired. In some embodiments, the acquisition of the preliminary parameter(s) may be performed by the preliminary calculation module 401. In some embodiments, the acquisition of the preliminary parameter(s) may be performed by the acquisition module of the parameter setting engine 201. In some embodiments, the preliminary parameter(s) may be acquired from the storage engine 204, or from the database 105. In some embodiments, the preliminary parameter(s) may be acquired from user input. In step 505, the acquired preliminary parameter(s) may be stored in the storage engine 204, or in the database 105.

In step 502, a preliminary calculation may be performed to provide one or more preliminary parameter. The preliminary calculation may be performed by the preliminary calculation module 401. In some embodiments, the preliminary calculation may be performed based on the preliminary parameter(s) acquired in step 501. In step 504, at least some of the preliminary parameter(s) may be outputted. At least some of the preliminary parameter(s) may be used to configure, for example, the image device 101, an imaging system, or a portion thereof. In step 505, at least some of the preliminary parameter(s) may be stored in the storage engine 204, or in the database 105.

In step 503, a secondary calculation may be performed to provide one or more secondary parameters. The step 503 of the secondary calculation may be optional. Merely by way of example, if the preliminary parameter(s) satisfy/satisfies a rule, the secondary calculation may be skipped, and the preliminary parameters may be outputted in step 504. In some embodiments, if the preliminary parameters satisfy a rule, the secondary calculation may still be performed. For instance, if the preliminary parameters satisfy a first rule, the secondary calculation may be performed according to a second rule. The first rule and the second rule may be different or the same. The second rule may be part of the first rule. The first rule and the second rule may be different or the same. The second rule may be part of the first rule.

In some embodiments, if the preliminary parameters do not satisfy a rule, the secondary calculation may be performed in step 503 and one or more secondary parameters may be obtained. The secondary calculation may be performed based on a rule. For instance, if the preliminary parameters do not satisfy a first rule, the secondary calculation may be performed according to a second rule. The first rule and the second rule may be different or the same. The second rule may be part of the first rule.

In step 504, the secondary parameter(s) may be outputted. At least some of the secondary parameters may be used to configure, for example, the imaging device 101. In step 505, at least some of the secondary parameter(s) may be stored in the storage engine 204, or in the database 105.

Figure 6:
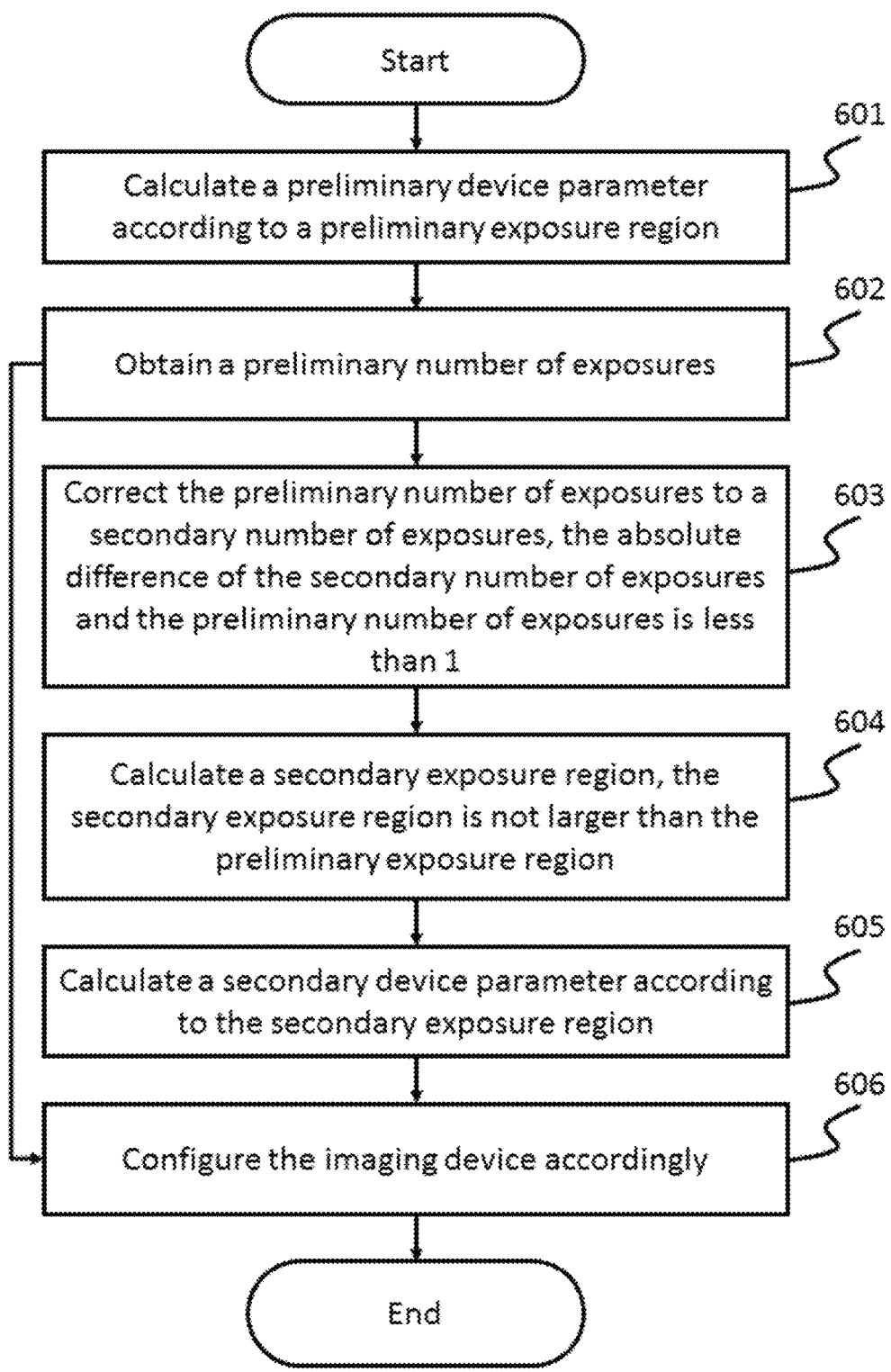
FIG. 6 is a flowchart of another exemplary process for setting parameters according to some embodiments of the present disclosure.

FIG. 6 is a flowchart of an exemplary process for setting parameters according to some embodiments of the present disclosure. As illustrated, FIG. 6 is an exemplary process for setting parameters according to some embodiments where an X-ray examination is desired. It should be noted that the flowchart described below is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure.

Beginning in step 601, a preliminary device parameter may be calculated according to a preliminary exposure region. Step 601 may be performed by the preliminary calculation module 401. Exemplary preliminary device parameters may include the number of exposures, the overlapping region between two adjacent exposures, the starting position of the effective light field, the stopping position of the effective light field, the height of the effective light field, etc. In some embodiments, the preliminary exposure region may be designated by a user. In some embodiments, the preliminary exposure region may be provided during initialization of the imaging device. A preliminary number of exposures may be obtained in step 602. The preliminary number of exposures may be obtained based on, for example, the preliminary exposure region. The preliminary number of exposures may be obtained by the preliminary calculation module 401. The obtained preliminary number of exposures may be compared to a rule. If the preliminary number of exposures satisfies the rule, the remaining steps of the process may be skipped, and the preliminary device parameters, including the preliminary exposure region, may be outputted by the parameter setting engine 201. The preliminary device parameters may be used to configure an imaging device, for example, the imaging device 101, as shown in step 606.

In some embodiments, the rule specifies that the number of exposures is an integer. In some embodiments where the calculated preliminary number of exposures is an integer, one or more of the remaining steps illustrated in FIG. 6 may be skipped. In some embodiments where the calculated preliminary number of exposures is an integer, one or more of the remaining steps illustrated in FIG. 6 may still be performed. In some embodiments where the calculated preliminary number of exposures is an integer, one or more secondary parameters may be set equal to the preliminary parameters.

In some embodiments where the calculated preliminary number of exposures is not an integer, the preliminary number of exposures may be adjusted to provide a secondary number of exposures according to step 603. The step 603 may be performed by the secondary calculation module 402. For instance, the preliminary number of exposures may be rounded to the preceding integer or the next integer such that the difference between the secondary number of exposures and the preliminary number of exposures is less than 1. In some embodiments, the adjustment of the preliminary number of exposures may be performed in accordance with a threshold. See, for example, the description in connection with FIG. 11.

After obtaining a secondary number of exposures, a secondary exposure region may be calculated based on the secondary number of exposures in step 604. The secondary exposure region may be calculated such that the secondary exposure region is not larger than the preliminary exposure region. See, for example, the description in connection with FIG. 11.

In step 605, a secondary device parameter may be calculated according to the secondary exposure region. A non-exclusive list of secondary device parameters may include: the overlapping region between two adjacent exposures, the starting position of the effective light field, the stopping position of the effective light field, the height of the effective light field, etc. In some embodiments, the imaging device 101 may be configured according to the secondary device parameters and/or the secondary exposure region in step 606. In some embodiments, the imaging device 101 may be configured according to the preliminary parameters in step 606.

Figure 7:
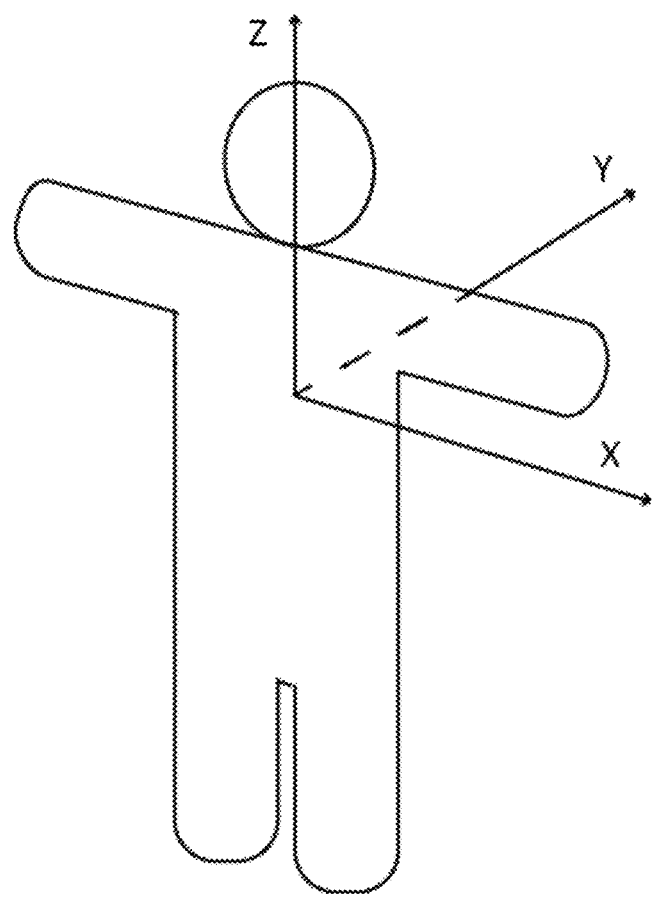
FIG. 7 illustrates a schematic view of the Left, Posterior, Superior (LPS) coordinate system used in connection with some embodiments of the present disclosure.

FIG. 7 illustrates a schematic view of the Left, Posterior, Superior (LPS) coordinate system used in connection with some embodiments of the present disclosure. As shown in FIG. 7, the X-Y-Z axis may define a three dimensional space such that the origin of it may be located within a target body, for example, within the chest of a patient. One of the three axes may be perpendicular to the other two. The positive direction of each one of the three axes is illustrated in FIG. 7. The x-axis may point from the right towards the left with respect to the patient. The Y-axis may point from the anterior towards the posterior, i.e., from the front towards the back, with respect to the patient. The Z-axis may point from the inferior towards the superior, i.e., from the feet towards the head, with respect to the patient.

Particularly, each two of the X axis, the Y axis, and the Z axis may define a plane perpendicular to the other planes defined by the other combinations of the three axes. Therefore, the three dimensional space defined by the X axis, the Y axis, and the Z axis may include three planes that may be used to describe an anatomical position of or within the patient. Particularly, the X axis and the Y axis may define a plane that may be referred to as the axial plane or transverse plane. The axial plane or transverse plane may separate the head (superior) from the feet (inferior). The axial plane or transverse plane may be substantially parallel to the ground when a patient is standing, for example, in front of an imaging device. The axial plane or transverse plane may be substantially perpendicular to the ground when the patient is lying or lying in prone on a table.

The X axis and the Z axis may define a plane that may be referred to as the coronal plane. The coronal plane may separate the front (anterior) from the back (posterior). The coronal plane may be substantially perpendicular to the ground when a patient is standing, for example, in front of an imaging device. The coronal plane may be substantially parallel to the ground when the patient is lying or lying in prone on a table.

The Y axis and the Z axis may define a plane that may be referred to as the sagittal plane or longitudinal plane. The sagittal plane or longitudinal plane may separate the left from the right from the left. The sagittal plane or longitudinal plane may be substantially perpendicular to the ground when a patient is standing, for example, in front of an imaging device. The sagittal plane or longitudinal plane may be substantially perpendicular to the ground when the patient is lying or lying in prone on a table.

It should be noted that the coordinate system described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure.

The LPS coordinate system may be used in connection with the Digital Imaging and Communications in Medicine (DICOM) standard. The DICOM is a standard for handling, storing, printing, and transmitting information in medical imaging. The DICOM may include a file format definition and a network communication protocol. In some sections of the DICOM standard, it specifies image plane module attributes and image plane attribute descriptions including, for example, image position and image orientation. A DICOM file may be exchanged between two entities that may receive images and/or patient data in DICOM format. DICOM may enable the integration of scanners, servers, workstations, printers, and network hardware from multiple manufacturers into a picture archiving and communication system (PACS). DICOM is known as NEMA standard PS3, and as ISO standard 12052:2006 "Health informatics—Digital imaging and communication in medicine (DICOM) including workflow and data management." It should be noted that the standard described above is provided for the purposes of illustration, and not intended to limit the scope of the present disclosure. Apparently, the teaching of the present disclosure may be used in connection with any standards that it may comply, and for persons having ordinary skills in the art, numerous variations and modifications may be conducted under the teaching of the present disclosure. However, those variations and modifications do not depart the protecting scope of the present disclosure.

Figure 8:
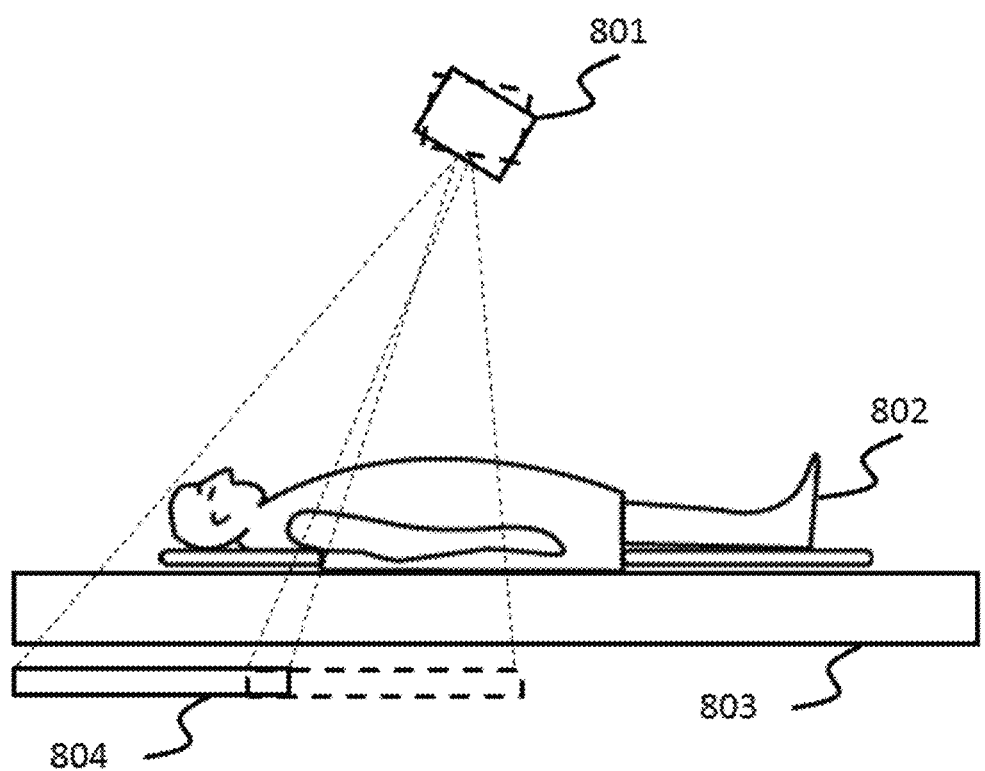
FIGS. 8 to 10 illustrate exemplary imaging systems according to some embodiments of the present disclosure.

FIG. 8 illustrates an imaging device 101 according to some embodiments of the present disclosure. The imaging device 101 illustrated in FIG. 8 is an X-ray imaging device. Non-exclusive examples of X-ray imaging devices that may be used in connection with some embodiments of the present disclosure include imaging devices used for computed tomography, fluoroscopy, radiography, etc.

As may be seen in the figure, the imaging device 101 may include a tube 801 that may generate a beam of X-ray used for imaging. The tube 801 may constitute an X-radiation source. The tube 801 may assume different configurations compatible with the present disclosure. A non-exclusive list of exemplary tubes that may be used in connection with the present disclosure include a rotating anode tube, a solid-anode microfocus X-ray tube, a metal-jet-anode microfocus X-ray tube, etc. The tubes that may be used in connection with the image composition system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments of the present disclosure, the tube 801 may be mounted proximal to a beam limiting device (not shown in the figure). The beam limiting device may function to define the beam of X-rays generated by the tube 801. As used herein, "to define" may mean either to cause the directions of at least some of the X-rays of the beam to align in a specific direction, or to define the spatial cross section of the beam. In some embodiments, a beam limiting device may filter a plurality of X-rays so that only those traveling in a specified direction may be allowed through the beam limiting device. The beam limiting device, in some embodiments, the width of the beam of X-rays generated by the tube 801 may be defined by the beam limiting device such that the height of the effective light field may equal to a product of the opening of the beam limiting device in the vertical direction and a constant k.

Particularly, as may be seen in the figure, a target body 802 may be placed on a table 803. The target body 802 may be a patient. In some embodiments, the table 803 may slide or move along in one and/or multiple directions. In some embodiments, the height of the table 803 may be adjusted. The adjustment of the height of the table 803 may be realized by an upward and/or a downward movement of the table. In some embodiments, the height of the table 803 may be adjusted before an imaging operation commences. In some embodiments, the height of the table 803 may be adjusted before an exposure of an imaging operation is taken. The adjustment of the height of the table 803 may accommodate target bodies of different sizes.

A detector (or referred to as radiation detector) 804 may be configured to detect an X-ray emitted from the tube 801 that passes through a target body. In some embodiments of the present disclosure, the detector 804 may be placed underneath the table 803. In alternative embodiments, the detector 804 may be placed beneath the target body 802 and above the table 803. Yet in other embodiments, the detector 804 may be placed inside the table 803 as long as it may receive X-ray signals. The detector 804 may assume different configurations that may be compatible with the present disclosure. A non-exclusive list of exemplary detectors that may be used in connection with the present disclosure includes: a gas ionization detector, a gas proportional detector, a multiwire and microstrip proportional chamber, a scintillation detector, an energy-resolving semiconductor detector, a current-mode semiconductor detector, a CCD detector, a microchannel plate detector, an image plate detector, an X-ray streak camera, a photographic film, and other X-ray detectors such as one operating at a superconducting temperature. The detectors that may be used in connection with the image composition system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments of the present disclosure where a long-length image and/or the scan of the whole body is desired, multiple exposures may be needed to generate a composite image. As shown in the figure in solid lines, the tube 801 may be placed in a first angle with reference to the axis perpendicular to the ground. The detector 804 may be placed in a first position under the head (superior) of the human patient 802. An X-ray beam generated by the tube 801 in the first angle may be received by the detector 804 placed in the first position under the head (superior) of the target body 802. Hence the first image may be generated for a first exposure area of the target body 802. After the generation of the first image, the tube 801 may turn a particular angle to be positioned at a second angle (as shown by the dashed line in the figure) with reference to the axis perpendicular to the ground. The detector 804 may move a particular distance along the bed towards the feet (interior) of the target body 802 to be positioned at a second position (as shown in the dashed line in the figure), such that an X-ray beam generated by the tube 801 in the second position may be received by the detector 804 in the second position. The second image may be generated for a second exposure area of the target body 802. In some embodiments where more than two exposures are desired, the image composition system may repeat the process and generate a series of images. In some embodiments, two adjacent sub-images generated by the process described above may have an overlapping region. The area of the overlapping regions between a pair of the adjacent sub-images are substantially the same. Description regarding the determination of an overlapping region in the two adjacent sub-images may be found elsewhere in the present disclosure. See, for example, FIG. 11 and the description thereof.

In some embodiments, the tube 801 and the detector 804 may move simultaneously and/or in a synchronized fashion. In some embodiments, the tube 801 and the detector 804 move sequentially; either one may move prior to the other. In some embodiments, the position of the tube 801 may be adjusted manually. In some embodiments, the position of the tube 801 may be adjusted automatically. In some embodiments, the position of the detector 804 may be adjusted manually. In some embodiments, the position of the detector 804 may be adjusted automatically. In some embodiments, the position of the tube 801 and the position of the detector 804 may be adjusted in a similar manner, either manually or automatically. In some embodiments, the position of the tube 801 and the position of the detector 804 may be adjusted in different manners; one may be adjusted manually, and the other may be adjusted automatically.

The imaging device 101 may include a structure to facilitate the adjustment of, for example, the tube 801, the detector 804, etc. The structure may include one or more components the movement of which may achieve the adjustment. The structure may include, for example, a slidable handle, a rotatable handle, or the like, or a combination thereof, to allow manual adjustment. The structure may be controlled by, for example, a control signal to allow automatic adjustment. Merely by way of example, a user (for example, a healthcare provider, an imaging specialist, etc.) may provide an instruction via, for example, an input device; a control signal may be generated based on the instruction. In some embodiments, the instruction may include one or more preliminary device parameter as described elsewhere in the present disclosure.

It should be noted that the motion of the tube 801 and the detector 804 described above is provided for the purposes of illustration, and not intended to limit the scope of the present disclosure. Apparently for persons having ordinary skills in the art, numerous variations and modifications may be conducted under the teaching of the present disclosure. However, those variations and modifications do not depart the protecting scope of the present disclosure.

Figure 9:
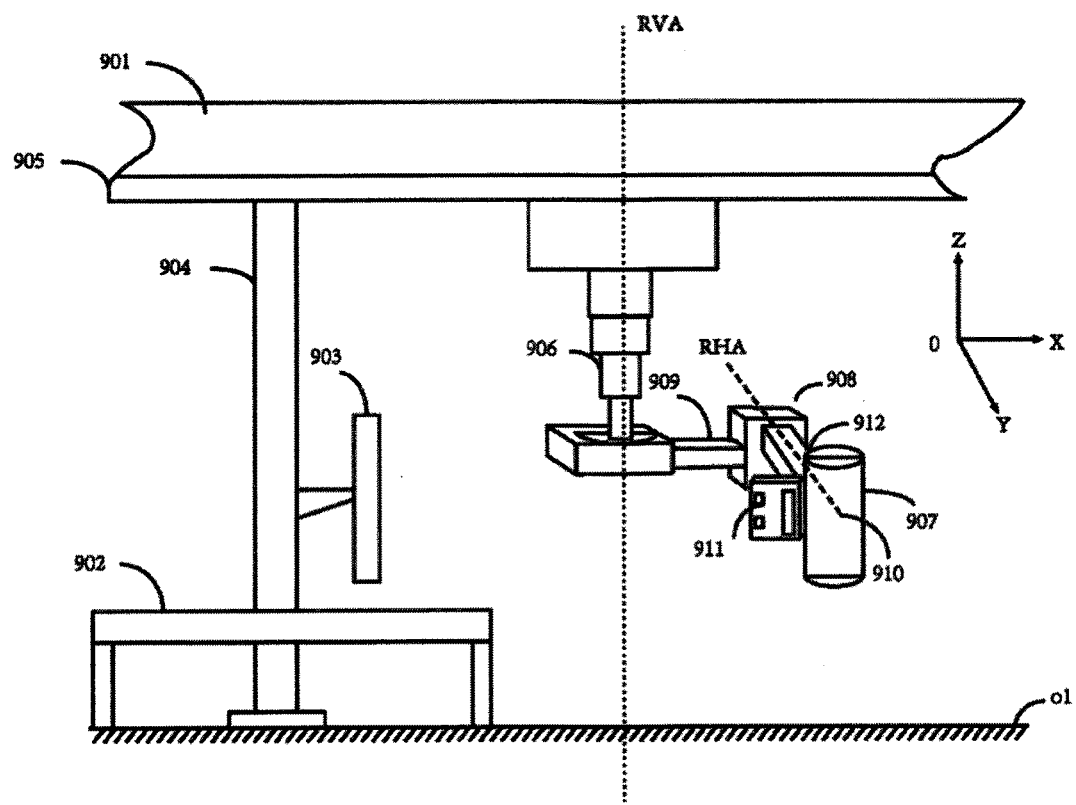
Figure 10:
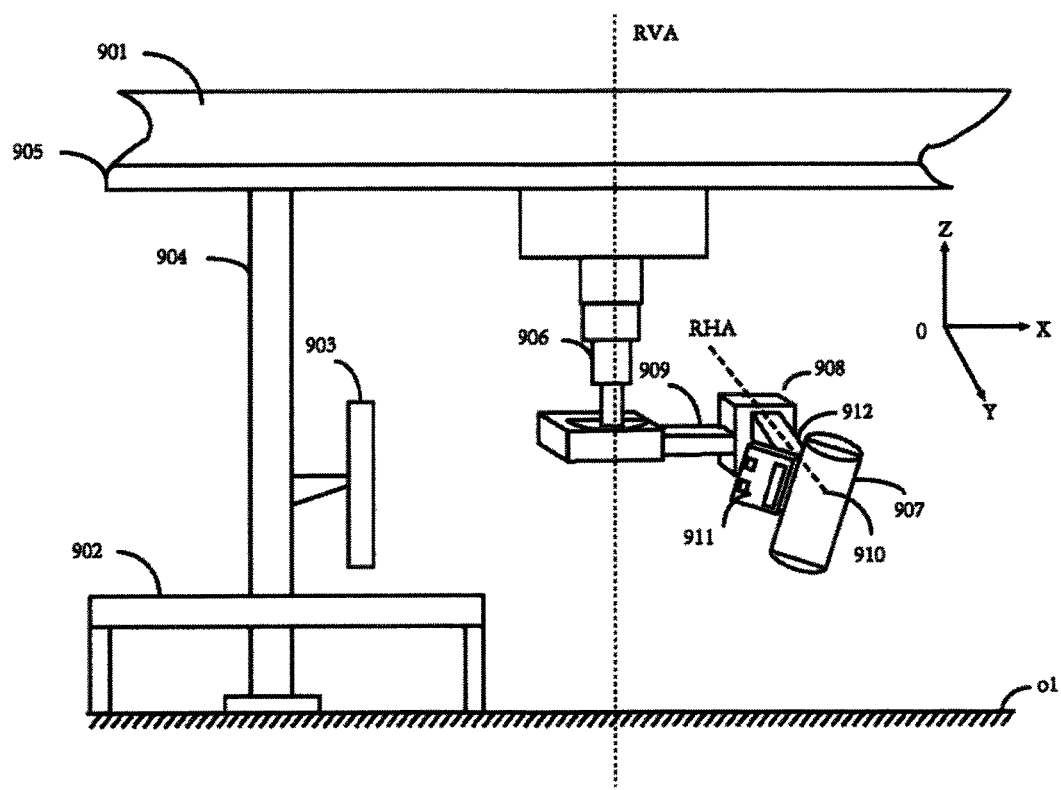

FIG. 9 and FIG. 10 illustrate another imaging device according to some embodiments of the present disclosure. The imaging device illustrated in FIG. 9 and FIG. 10 is an X-ray imaging device. FIG. 9 illustrates the configuration of the imaging device in a first moment. FIG. 10 illustrates the configuration of the imaging device in a second moment. As shown in the figures, the imaging device includes a beam 901, a table 902, a detector 903, a vertical stand 904, a moving guide 905, a ceiling suspension 906 capable of extending and contracting in the vertical direction, and a tube 907. In some embodiments, the vertical stand 904 may be installed on the ground plane o1. As may be seen in the figures, the XY-plane in the three dimensional coordinates may be parallel to the ground plane o1. Upon the vertical stand 904, the detector 903 may be mounted. In some embodiments, the tube 907 may be mounted proximal to a beam limiting device 911.

As may be seen in the figure, the detector 903 may move up and/or down along the vertical stand 904. The tube 907 may be connected to the ceiling suspension 906 via a tube support 908. In some embodiments, via the tube support 908, the tube 907 may be rotated within the XY-plane and/or the XZ-plane. In some embodiments, via the tube support 908, the tube 907 may move in the vertical direction. The ceiling suspension 906 may extend or contract in the vertical direction. The tube support 908 may include a first support structure 909 and a second support structure 912. The first support structure 909 may be at an angle with the second support structures 912. Merely by way of example, the first support structure 909 may be perpendicular to the second support structure 912.

As may be seen in the figures, the central axis of the ceiling suspension 906 may be labeled as an RVA-axis. The RVA-axis may be parallel to the Z-axis. As may be seen in the figures, the central axis of the second support structure 912 may be labeled as an RHA-axis. The RHA-axis may be parallel to the Y-axis. In some embodiments, the first support structure 909 may allow the tube support 908 and the tube 907 to rotate about the RVA-axis within the XY-plane. In some embodiments, the second support structure 912 may allow the tube to rotate about the RHA-axis within the XZ-plane. As shown in FIG. 10 where the imaging device is configured in the second moment, the tube 907 may be tilted with reference to the Z-axis via the rotation of the second support structure 912 within the XZ-plane.

Figure 11:
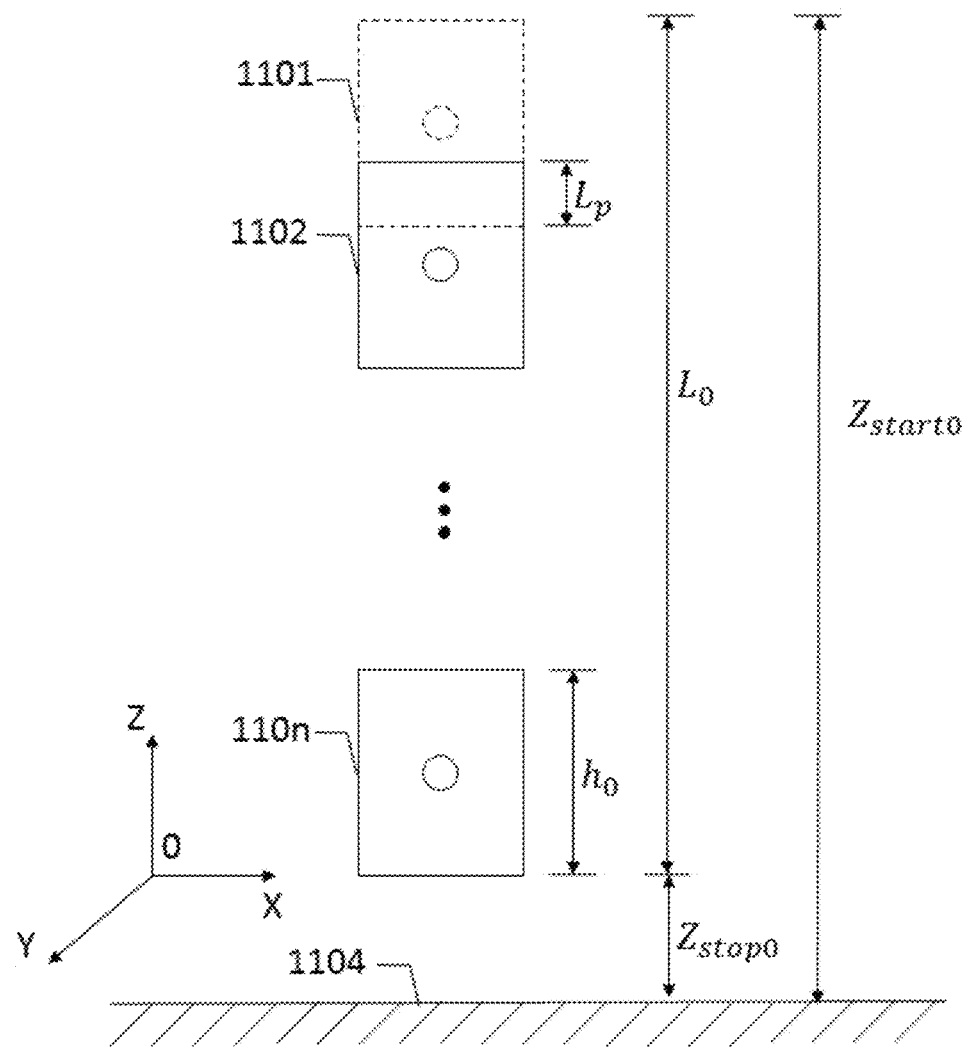
FIG. 11 illustrates a process for determining the number of exposures according to some embodiments of the present disclosure.

FIG. 11 illustrates a process for determining the number of exposures according to some embodiments of the present disclosure. As may be seen in FIG. 11, the dashed box 1101 may represent the position of the effective light field with respect to the first exposure. The upper edge of the dashed box 1101 may represent the starting position of the preliminary effective light field. The dashed box 110$n$ may represent the position of the effective light field with respect to the last exposure. The lower edge of the dashed box 110$n$ may represent the preliminary stopping position of the effective light field. The solid box 1102 may represent the position of the effective light field with respect to the second exposure. A portion of the solid box 1101 may at least partially overlap with the dashed box 1101. The height of the overlapping region may be denoted by $L_p$. The heights of the dashed boxes 1101 and 110$n$, and the height of the solid box 1102 may equal to the height of the preliminary effective light field $h_0$. The line 1190 may represent the ground plane.

According to some embodiments of the present disclosure where the preliminary number of exposures is an integer, the secondary number of exposures may equal to the preliminary number of exposures, and the secondary device parameters may be the same as the preliminary device parameters. The secondary exposure region may be the same as the preliminary exposure region. According to some embodiments of the present disclosure where the preliminary number of exposures is not an integer, based on the rate in the change of the composing length, the secondary number of exposures may be the largest integer not greater than the preliminary number of exposures, or may be the largest integer not greater than the preliminary number of exposures plus 1.

According to some embodiments of the present disclosure where the preliminary number of exposures is the largest integer not greater than the preliminary number of exposures, the starting position and stopping position of the effective light field may be adjusted such that the secondary exposure region between the secondary starting position and the secondary stopping position of the effective light field is not greater than the preliminary exposure region.

According to some embodiments of the present disclosure where the preliminary number of exposures is the largest integer not greater than the preliminary number of exposures plus 1, the secondary starting position and the secondary stopping position of the effective light field may be the same as the preliminary exposure region while the secondary height of the effective light field is not greater than the preliminary height of the effective light field. Details regarding the above description will be further explained below.

As may be seen in FIG. 11, the distance of the preliminary starting position of the effective light field from the ground plane may be $Z_{start0}$, and the distance of the preliminary stopping position of the effective light field from the ground plane is $Z_{stop0}$. Based on the preliminary starting position and the preliminary stopping position of the effective light field, the preliminary composing length $L_0$ of the image composition may equal to:

$$L_0 = Z_{start0} - Z_{stop0}. \tag{001}$$

Based on the preliminary composing length $L_0$ and the length of the overlapping region between the two adjacent exposure $L_p$, a preliminary number of exposures Y may be calculated according to the following equation:

$$Y=(L_0-L_p)/(h_0-L_p). \tag{002}$$

In some embodiments of the present disclosure, the preliminary number of exposures Y obtained via Equation (002) may be an integer. In such embodiments, the preliminary number of exposures Y may not need to be adjusted. The secondary number of exposures may be set equal to the preliminary number of exposures Y. In some embodiments of the present disclosure, the preliminary number of exposures Y obtained via Equation (002) is not be an integer. In such embodiments, the preliminary number of exposures Y may be adjusted and a secondary number of exposures that is an integer may be obtained. Various methods may be used to adjust the preliminary number of exposures to an integer. For example, the integer part of the preliminary number of exposures Y may be designated as the secondary number of exposures. As another example, the integer part of the preliminary number of exposures Y plus 1 may be designated as the secondary number of exposures. The adjustment methods that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments where the preliminary number of exposures Y is not an integer, the secondary number of exposures may be adjusted according to a rate of change in the composing length. For instance, the rate of change in the composing length may depend on the preliminary composing length and a secondary composing length. Merely by way of example, the rate of change in the composing length may be calculated according to the following equation:

$$P=(L_0-L_1)/L_0, \tag{003}$$

where P represents the rate of change in the composing length, $L_0$ represents the preliminary composing length, and $L_1$ represents the secondary composing length. The secondary composing length may be calculated according to the following equation, $$L_1=\text{floor}(Y)\times(h_0-L_p)+L_p, \tag{004}$$

where the function floor(x) is the largest integer not greater than x.

The rate of change in the composing length may be compared with a threshold to determine the secondary number of exposures such that the difference of the secondary number of exposures and the preliminary number of exposures is less than 1.

In some embodiments of the present disclosure, when the rate of change in the composing length is less than or equal to the threshold, the remnant composing length for the last exposure may be less than the height of the effective light field, the impact of which on the image composition may be considered insignificant. Then the secondary number of exposures may be set equal to floor(Y) and the fractional part of the preliminary number of exposures may be discarded. In some embodiments where the rate of change in the composing length is greater than the threshold, the remnant composing length for the last exposure may be less than the height of the effective light field, the impact of which on the image composition may be considered significant. Then the fractional part of the preliminary number of exposures may be retained. The secondary number of exposures may equal to floor(Y)+1.

In some embodiments of the present disclosure, the threshold may be set within the range of 3% to 7%. More particularly, in some embodiments, the threshold may be 5%. In some embodiments, the threshold may be 6% or 7%. Yet in other embodiments, the user may adjust the threshold based on the clinical needs at his discretion.

The methods of determining a number of exposures that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments of the present disclosure, the preliminary number of exposures is an integer. In such an occasion, it may be unnecessary to adjust one or more preliminary device parameters. The imaging device may be configured according to those preliminary parameters. Alternatively, the secondary device parameters may be set equal to the preliminary parameters, and the imaging device may be configured according to obtain such secondary device parameters. In some embodiments of the present disclosure, the preliminary number of exposures is not an integer, the preliminary device parameters may be adjusted to provide secondary device parameters. As discussed above, the secondary number of exposures may be set equal to floor(Y) or floor(Y)+1, and the secondary device parameters may be adjusted according to the secondary number of exposures.

In some embodiments where the secondary number of exposures equals to floor(Y), the secondary number of exposures may be less than the preliminary number of exposures. For instance, the secondary composing length may equal to the preliminary composing length:

$$L_1=\text{floor}(Y)\times(h_0-L_p)+L_p. \tag{005}$$

The secondary composing length corresponding to the secondary number of exposures may be shorter than the preliminary composing length corresponding to the preliminary number of exposures. Therefore, the preliminary starting position and preliminary stopping position of the effective light field may be adjusted to provide a secondary starting position and a secondary stopping position of the effective light field, respectively. The distance between the starting position and the stopping position of the effective light field may be the secondary composing length.

In some embodiments of the present disclosure where the secondary number of exposures equals to floor(Y), the secondary starting position $Z_{start}$ and the secondary stopping position $Z_{stop}$ of the effective light field corresponding to the secondary device parameters may be obtained respectively using the following equations, respectively:

$$Z_{start}=Z_{start0}-(L_0-L_1)/2; \tag{006}$$

and, $$Z_{stop}=Z_{stop0}+(L_0-L_1)/2, \tag{007}$$

where the height of the effective light field may be equal to the preliminary height of the effective light field $h_0$.

In some embodiments where the secondary number of exposures equals to floor(Y)+1, the secondary exposure region may be set equal to the preliminary exposure region such that the secondary composing length equals to the preliminary composing length. Therefore, the starting position and the stopping position of the effective light field do not need to be adjusted. Instead, the height of the effective light field may be adjusted to achieve the number of exposures of floor(Y)+1. The secondary height of the effective light field may be less than the preliminary height of the effective light field.

Merely by way of example where the secondary number of exposures equals to floor(Y)+1, the secondary starting position of the effective light field is set to be the preliminary starting position of the effective light field $Z_{start0}$, and the secondary stopping position of the effective light field is set to be the preliminary stopping position of the effective light field $Z_{stop0}$, the secondary height of the effective light field may be obtained using the following equation:

$$h = L_p + (L_0 - L_p)/(\text{floor}(Y)+1) \quad (008)$$

In some embodiments of the present disclosure where a series of X-ray images are generated, the secondary exposure region may be equal to or smaller than the preliminary exposure region. Hence, the radiation dose received by the target body, for example, a human patient, may be reduced. In some embodiments of the present disclosure, the determination of the secondary number of exposures may depend on a rate of change in the composing length. The composite image may satisfy practical clinical demands regardless of whether the secondary number of exposures equal to floor (Y) or floor(Y)+1.

The process for determining a device parameter that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments of the present disclosure, the secondary number of exposures may be the same as the preliminary number of exposures. In some embodiments, the secondary number of exposures may be the largest integer not greater than the preliminary number of exposures. In some embodiments, the secondary number of exposures may be the largest integer not greater than the preliminary number of exposures plus 1. And various secondary device parameters may be applied according to different secondary number of exposures. In some embodiments, the position of the detector and the tube rotation angle corresponding to an exposure may be obtained according to a secondary number of exposures and secondary device parameters.

In some embodiments of the present disclosure, the position of the detector at an exposure may be obtained. The distance between the X-ray generator (or another type of radiation source) and the detector (or the image-receptor) may be referred to as the source to image-receptor distance (SID, or S). The change of position of the focus of the tube 907 along Z-axis may be significantly smaller than the SID, such that the position of the focus of the tube 907 may be treated as approximately fixed along the Z-axis. The tube 907 may rotate about the RHZ-axis within the XZ-plane. In other words, during the imaging process, the distance between the focus of the tube 910 and the ground plane may be approximately fixed; the tube 907 may rotate about the RHA-axis via the second support structure 912 within the XZ-plane (with reference to FIG. 9 and FIG. 10). The detector 903 may move up and/or down along the vertical stand 904 in the Z-axis.

In some embodiments of the present disclosure where the preliminary number of exposures is an integer, the imaging device may be configured according to the preliminary device parameters. Alternatively, the secondary device parameters may be set to be the same as the preliminary device parameters, and the imaging device may be configured according to the secondary device parameters. The position of detector in the Z-axis may be obtained through the preliminary position of each exposures.

Returning to FIG. 11, the height of the overlapping region between two adjacent exposures may be $L_p$. The preliminary position of the first exposure may correspond to the upper edge of the effective light field corresponding to the first exposure. The preliminary position of the first exposure $Z_1$ along the Z-direction may be set to be $Z_{start0}$. The preliminary position of the second exposure may be the upper edge of the effective light field corresponding to the second exposure. The preliminary position of the second exposure $Z_2$ may be set to be:

$$Z_2 = Z_{start0} - h_0 + L_p. \quad (009)$$

Similarly, the preliminary position of the nth exposure may be the upper edge of the effective light field corresponding to the nth exposure. The position of the nth exposure $Z_n$ may be set to be:

$$Z_n = Z_{start0} - (n-1) \times h_0 + (n-1) \times L_p, \quad (010)$$

where n stands for the nth exposures.

As already described, the effective light field may be the light field received by the detector that may be effective to provide imaging information. Therefore, the position of the detector in the Z direction may be determined based on the effective light fields in the Z direction.

In some embodiments, the center of the detector may be considered as the position of the detector, and the position of the center of the detector may be determined according to the upper edge of a corresponding effective light field. With reference to FIG. 11, the position of the center of the detector corresponding to the first exposure may be determined according to:

$$Z_{FD1} = Z_1 - (h_0/2) = Z_{start0} - (h_0/2). \quad (011)$$

The position of the center of the detector corresponding to the second exposure may be determined according to:

$$Z_{FD2} = Z_2 - (h_0/2) = Z_{start0} - (3/2) \times h_0 + L_p. \quad (012)$$

Similarly, the position of the center of the detector corresponding to the nth exposure may be determined according to:

$$Z_{FDn} = Z_n - (h_0/2) = Z_{start0} - ((2 \times n-1)/2) \times h_0 + (n-1) \times L_p, \quad (013)$$

where n stands for the nth exposure. The methods of determining the position of detector that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments of the present disclosure, the tube rotation angle may refer to the difference of the angle between the axis of the tube corresponding to an exposure and the X-axis with respect to the XZ-plane, and the angle between the axis of the tube corresponding to the preceding exposure and the X-axis with respect to the XZ-plane. In some embodiments of the present disclosure, the tube rotation angle may refer to the angle that the tube rotates between an exposure and a preceding exposure. For example, the angle between the axis of the tube and the X-axis within the XZ-plane corresponding to an exposure equals to A, and the angle between the axis of the tube and the X-axis within XZ-plane corresponding to the preceding exposure equals to B, the tube rotation angle corresponding to the exposure may be α=A−B. With reference to FIG. 9 and FIG. 10, the angle between the tube axis and the X-axis is the angle between the tube 907 rotating about the RHA axis within the XZ plane and the X-axis.

Figure 12:
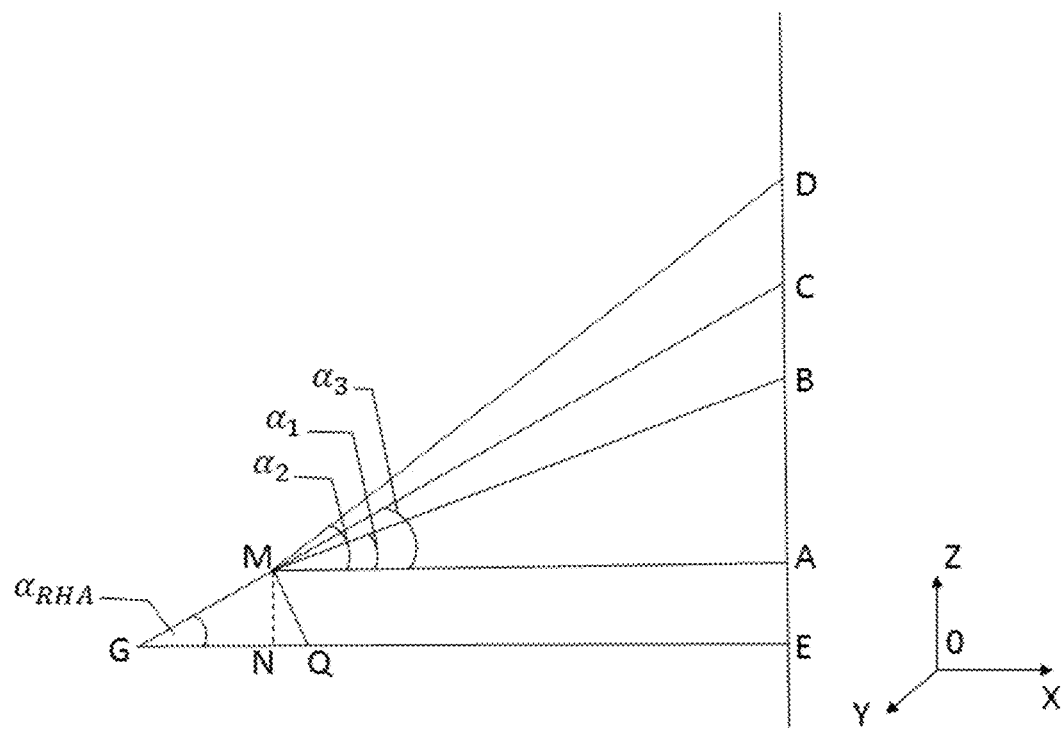
FIG. 12 illustrates a schematic view of the tube rotation angle corresponding to the nth exposure according to some embodiments of the present disclosure.

FIG. 12 illustrates a schematic view of the tube rotation angle corresponding to the nth exposure. As may be seen in FIG. 12, Point G may represent the point of the rotation axis of the tube. Point M and point Q may represent the positions of the focus of the tube corresponding to two adjacent exposures, respectively. The angle $\alpha_{RHA}$ between the GM and GQ may be the tube rotation angle corresponding to the nth exposure.

As illustrated in the FIG. 12, the point of the rotation axis of the tube G may intersect with the detector at point E in the X-axis direction. The focus of the tube M may intersect with the detector at point A in the X-axis direction. The effective light field that the tube projects to the detector may be between point D and point B. Point C may be the intersection of the detector and the perpendicular bisector of the rays emitted by the tube G. MN may intersect with the horizontal line perpendicularly at N. The angle between MA and MD may be $\alpha_2$, the angle between MA and MB may be $\alpha_1$, and the angle between MA and MC may be $\alpha_3$.

The distance between point Q and point E may be the SID, $S_{SID}$. With reference to FIG. 12, $$MA = QE + NQ = QE + GM \times (1 - \cos a_{RHA}). \quad (014)$$

In some embodiments, the length of GM may be significantly greater than the length of QE, such that:

$$GM \times (1 - \cos a_{RHA}) = 0, \quad (015)$$

and, $$MA = QE \quad (016)$$

In other words, $$MA = S_{SID}. \quad (017)$$

The position of point M along the Z-axis direction may be $Z_{TCS}$. Point D may be the upper edge of the effective light field corresponding to the nth exposure. The position of point D along the Z-axis direction may be:

$$Z_n = Z_{start0} - (n-1) \times h_0 + (n-1) \times L_p. \quad (018)$$

Point B may be the lower edge of effective light field corresponding to the nth exposure. The position of point B along the Z-axis direction may be $Z_n - h_0$. The following equations may be obtained according to the above description:

$$DA = Z_n - Z_{TCS} \quad (019)$$

and, $$BA = DA - h_0 = Z_n - Z_{TCS} - h_0. \quad (020)$$

With reference to FIG. 11, $$\alpha_{RHA} = \alpha_3 = (\alpha_1 + \alpha_2)/2, \quad (021)$$

wherein $$\alpha_1 = \arctan \frac{BA}{MA},$$

and $$\alpha_2 = \arctan \frac{DA}{MA}.$$

Substitute $$\alpha_1 = \arctan \frac{BA}{MA}$$

and
to Equation 021, then, $$\alpha_2 = \arctan \frac{DA}{MA}$$

$$\alpha_{RHA} = (\alpha_1 + \alpha_2)/2 = \frac{1}{2} \times \left( \arctan \frac{BA}{MA} + \arctan \frac{DA}{MA} \right) \quad (022)$$

$$a. = \frac{1}{2} \times \arctan \left[ \left( \frac{DA}{MA} + \frac{BA}{MA} \right) \Big/ \left( 1 - \frac{DA}{MA} \times \frac{BA}{MA} \right) \right]$$

$$b. = \frac{1}{2} \times \arctan \left[ \frac{MA \times (DA + BA)}{MA^2 - DA \times BA} \right].$$

Substitute $MA = S_{SID}$, $DA = Z_n - Z_{TCS}$, $BA = DA - h_0 = Z_n - Z_{TCS} - h_0$ into Equation 022, $$\alpha_{RHA} = \frac{1}{2} \times \arctan \left[ \frac{S_{SID} \times (|Z_n - Z_{TCS}| + |Z_n - Z_{TCS} - h_0|)}{S_{SID}^2 - (|Z_n - Z_{TCS}| \times |Z_n - Z_{TCS} - h_0|)} \right], \quad (023)$$

where $\alpha_{RHA}$ may be the difference of the angle between the axis of the tube corresponding to the nth exposure and the X-axis within the XZ-plane, and the angle between the axis of the tube corresponding to the (n−1)th exposure and the X-axis within the XZ-plane.

In some embodiments of the present disclosure where the secondary number of exposures is less than the preliminary number of exposures, the imaging device may be configured according to the secondary device parameters. The positions of the detector and the rotation angles of the tube may be determined in a process similar to that described above in connection with some embodiments of the present disclosure where the preliminary number of exposures is an integer.

As discussed above, in some embodiments where the secondary number of exposures is larger than the preliminary number of exposures, the secondary starting position and secondary stopping position of the effective light field may be the same as the preliminary starting and stopping position of the effective light field. The secondary height of the effective light field may be different from the preliminary height of the effective light field, and may be denoted as h. When calculating the position of the center of the detector and the tube rotation angles, the preliminary height of the effective light field in relevant parameters may be substituted by the secondary height of the effective light field. For instance, the position of the detector corresponding to each exposure may be:

$$Z_{FDn}=Z_{start0}-((2n-1)/2)\times h+(n-1)\times L_p, \quad (024)$$

and the tube rotation angle corresponding to each exposure may be:

$$\alpha_{RHA} = \frac{1}{2} \times \arctan\left[\frac{S_{SID} \times (|Z_n + Z_{TCS}| + |Z_n - Z_{TCS} - h|)}{S_{SID}^2 - (|Z_n - Z_{TCS}| + |Z_n - Z_{TCS} - h|)}\right] \quad (025)$$

where, $$Z_n=Z_{start0}-(n-1)\times h+(n-1)\times L_p, \quad (026)$$

$$h=L_p+(L_0-L_p)/(\text{floor}(Y)+1), \quad (027)$$

and, $$L_0=Z_{start0}-Z_{stop0} \quad (028)$$

The methods of determining the positions of the detector and tube that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

In some embodiments, in the clinical practice, a user may input one or more preliminary device parameters and the height of the overlapping region based on a preliminary exposure region. In some embodiments, the preliminary device parameters may be provided by the image composition system during initialization. The image composition system may calculate a preliminary number of exposures according to the inputs and obtain a secondary number of exposures and a secondary device parameter. During imaging, the user may designate a starting position and stopping position of the effective light field according to those secondary parameters. In some embodiments, the designation may be performed under the instruction of the user. In other embodiments, the image composition system may perform the designation automatically. The position of the detector corresponding to an exposure may be obtained according to the position of the effective light field. The image composition system may position the tubes, the detector, and/or the beam limiting devices accordingly and generate a series of images for composition.

In some embodiments, a preliminary number of exposures may be obtained based on a preliminary exposure region. A secondary number of exposures may be obtained based on the preliminary number of exposures, as well as a secondary device parameter, such that the secondary exposure region corresponding to the secondary number of exposures may be equal to or smaller than the preliminary exposure region, and that the absolute difference between the preliminary number of exposures and the secondary number of exposures may be less than 1. In some embodiments, in clinical practice, the number of exposures may be an integer. Under such circumstances, the system and process according to some embodiments of the present disclosure may help avoid that the secondary number of exposures may be greater than the preliminary number of exposures and reduce the radiation dose the patient may be exposed to.

In some embodiments of the present disclosure, the position of the tube along the z-axis may be approximately fixed, and the rotation of the tube may be confined within the XZ-plane. The position of the detector may be adjusted along with the rotation of the tube. In some embodiments, the detector may move along the Z-axis simultaneously with the rotation of the tube. In some embodiments, the motion of the detector and the rotation of the tube may be performed one after another.

In some embodiments of the present disclosure, a composite image may be obtained. The image composition system may obtain a series of sub-images through adjusting the parameters that may be used to configure an imaging device. The image composition system may obtain the position of the effective light field corresponding to an exposure and the height of the overlapping region between two adjacent sub-images. The image composition system may obtain a composite image by combining adjacent sub-images according to the position of the effective light field corresponding to an exposure and the height of the overlapping region between two adjacent sub-images. The methods of obtaining a composite image that may be used in connection with the present system described above are not exhaustive and are not limiting. Numerous other changes, substitutions, variations, alterations, and modifications may be ascertained to one skilled in the art and it is intended that the present disclosure encompass all such changes, substitutions, variations, alterations, and modifications as falling within the scope of the present disclosure.

Figure 13:
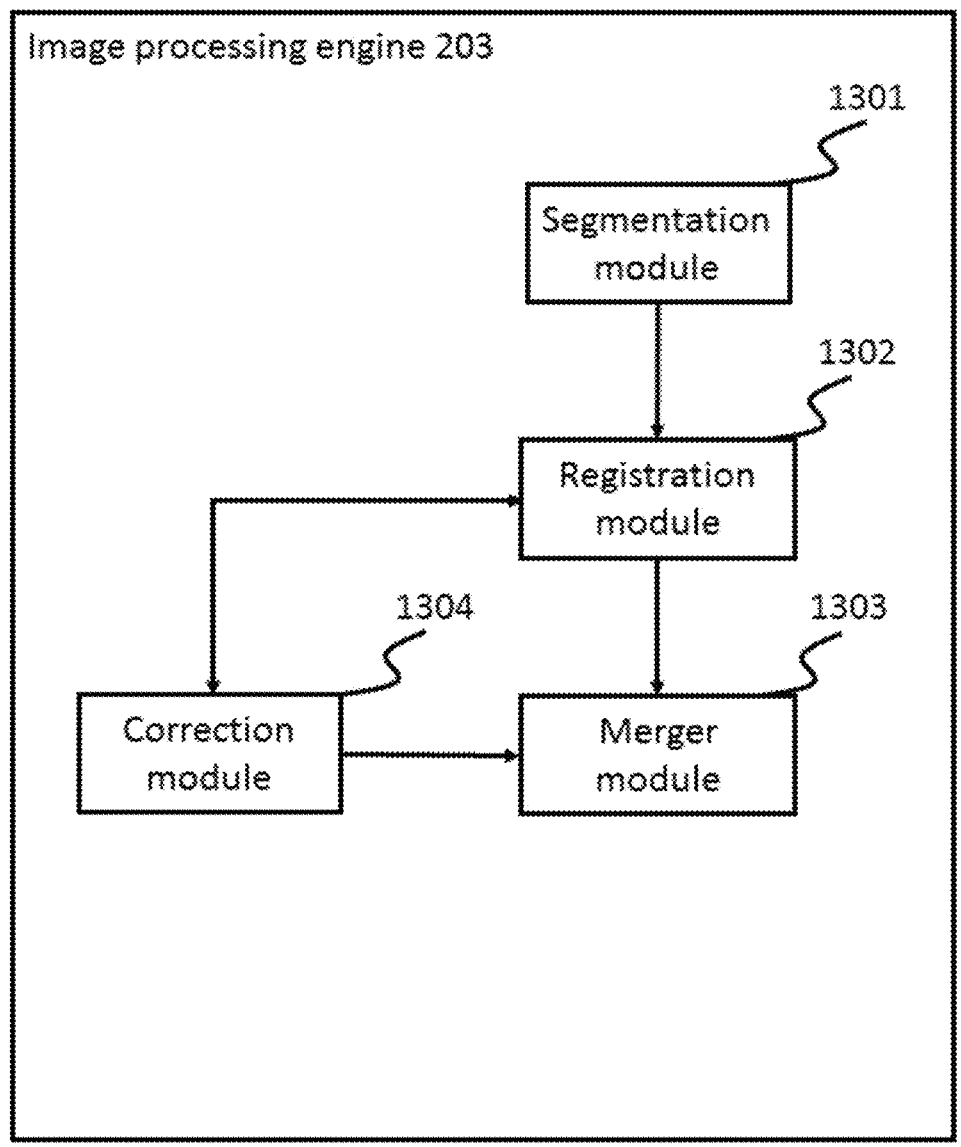
FIG. 13 is a block diagram illustrating an image processing engine according to some embodiments of the present disclosure.

FIG. 13 is a block diagram illustrating the image processing engine 203 according to some embodiments of the present disclosure. The image processing engine 203 may include a segmentation module 1301, a registration module 1302, a merger module 1303, and a correction module 1304. The segmentation module 1301 may be configured to segment one or more overlapping regions of 3D images received from the acquisition engine 202 (shown in FIG. 2) to produce overlapping images corresponding to 3D volume data. Optionally and preferably, the 3D images may be three-dimensional digital subtraction angiography images (3D-DSA images). Specifically, the 3D-DSA images may be 3D digital coronal images, 3D digital sagittal images, 3D digital transverse images, or the like, or a combination thereof. Alternatively, the segmentation module 1301 may be configured to segment images stored in storage module 204, the images may be, for example, 3D images, 2D images, or the like, or a combination thereof. Particularly, the 3D images may be 3D-DSA images. Optionally and preferably the 3D-DSA images may be 3D digital coronal images, 3D digital sagittal images, 3D digital transverse images, or the like, or a combination thereof. Merely by way of example, a series of scans may generate a plurality of sub-images to be combined together so that a composite image may be acquired, 2 adjacent sub-images may have an overlapping region, and the overlapping region of a sub-image may be segmented out by the segmentation module 1301. The overlapping region may be termed as overlapping image corresponding to 3D volume data. It should be noted that exemplary sub-images may be 3D images. Optionally and preferably, the 3D images may be 3D-DSA images. Specifically, the 3D-DSA images may be 3D digital coronal images, 3D digital sagittal images, 3D digital transverse images, or the like, or a combination thereof.

In some embodiments of the present disclosure, the segmentation may be performed in accordance with digital imaging and communication in medicine (DICOM). For instance, label (0020 0032) of DICOM may be utilized to segment overlapping regions out of 3D images corresponding to 3D volume data. It should be noted that the example described hereby is provided merely for the purposes of illustration, and should not be deemed to limit the scope of the present disclosure. Any number of overlapping regions of 3D images may be segmented by the segmentation module 1301. It should still be understood that any size of overlapping images of 3D images may be segmented by the segmentation module 1301, for example, 351*67*73, or 352*512*96. Furthermore, the segmentation module 1301 may also be configured to segment 2D images.

The segmented overlapping images corresponding to 3D volume data may be sent to the registration module 1302 for one or more registrations. The registration module 1302 may be configured to perform registrations including, for example, 2D registration, 3D registration, or the like, or a combination thereof. The registration may be performed to align two or more images into spatial alignment. The images may be taken, for instance, at different times, from different viewpoints, or from different modalities. Merely by way of example, the overlapping images corresponding to 3D volume data generated in the segmentation module 1301 may be registered by the registration module 1302. Afterwards, registered overlapping images corresponding to 3D volume data may be generated. The registered overlapping images corresponding to 3D volume data may be sent to the correction module 1304 for a fine registration, or to the merger module 1303 for image fusion to generate a composite image. The fine registration may include a process of optimization based on one or more algorithms. Exemplary algorithms may include recursion, a bisection method, an exhaustive method, a greedy algorithm, a divide and conquer algorithm, dynamic programming method, an iterative method, a branch-and-bound algorithm, a backtracking algorithm, or the like, or any combination thereof. The merger module 1303 may be configured to calibrate the sub-images based on the 3D registration, and the calibrated sub-images may be fused together to generate a composite image.

It should be understood that the description of the image processing engine 203 is merely provided for the purposes of illustration, and not intended to limit the scope of the present disclosure. For persons having ordinary skills in the art, numerous variations and modifications may be made under the teaching of the present disclosure. However, those variations and modifications do not depart from the protecting scope of the present discourse. For instance, the registered overlapping images corresponding to 3D volume data may be sent to the correction module 1304 and the merger module 1303 simultaneously or sequentially at any order. As still some instances, the correction module 1303 may be unnecessary. Sub-images that are not adjacent may have one or more overlapping regions as well.

Figure 14:
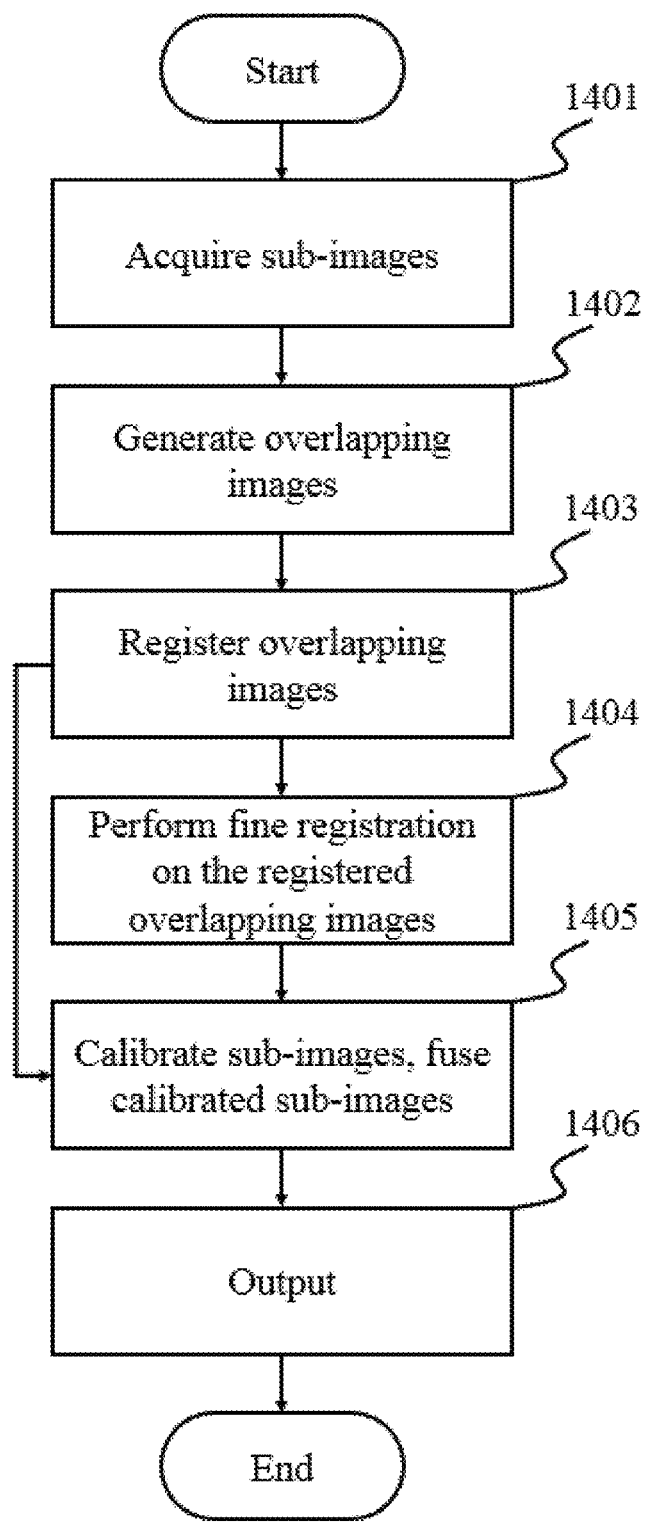
FIG. 14 is a flowchart illustrating a workflow of image processing according to some embodiments of the present disclosure.

FIG. 14 is a flowchart illustrating a workflow of image processing according to some embodiments of the present disclosure. In some embodiments of the present disclosure, sub-images of a region of interest (e.g., peripheral vessels of lower limbs) may be acquired in step 1401. The sub-images may be acquired by techniques including DSA (digital subtraction angiography), CT (computed tomography), CTA (computed tomography angiography), PET (positron emission tomography), X-ray, MM (magnetic resonance imaging), MRA (magnetic resonance angiography), SPECT (single-photon emission computerized tomography), US (ultrasound scanning), or the like, or a combination thereof. It should be noted that the sub-images may be 3D images, 2D images, or the like, or a combination thereof. Particularly, the 3D images may be 3D-DSA images. Optionally and preferably the 3D-DSA images may be 3D digital coronal images, 3D digital sagittal images, 3D digital transverse images, or the like, or a combination thereof.

Overlapping images corresponding to 3D volume data of the sub-images may be generated in step 1402. Merely by way of example, two adjacent sub-images acquired by two successive scans may have two overlapping images corresponding to 3D volume data of each sub-image, respectively. The two overlapping images corresponding to 3D volume data of the sub-images may be segmented and generated in step 1402.

Subsequently, the overlapping images corresponding to 3D volume data generated in step 1402 may be registered in step 1403. Specifically, exemplary reasons of the misalignment may include that the layout of the object being scanned is not perfectly parallel to the scanning plane of the imaging device; as a result, successive sub-images may be misaligned spatially. Other reasons may include, for example, the motion of a patient during the imaging procedure, the motion of an internal organ of the patient during the imaging procedure, the motion of the imaging device during the imaging procedure, or the like, or a combination thereof. The registration may include, a 2D registration, a 3D registration, or the like, or a combination thereof. Specifically, the process of a registration may include calculating one or more offsets and applying the offsets to reduce misalignment. The registered overlapping images corresponding to 3D volume data may be stored in the storage engine 204.

In step 1404, a fine registration may be performed on the registered overlapping images corresponding to 3D volume data. The fine registration may include a process of optimization based on one or more algorithms. Exemplary algorithms may include recursion, a bisection method, an exhaustive method, a greedy algorithm, a divide and conquer algorithm, dynamic programming method, an iterative method, a branch-and-bound algorithm, a backtracking algorithm, or the like, or any combination thereof. Results generated by the fine registration (e.g., one or more offsets) may be utilized to register the overlapping image corresponding to 3D volume data again. It should be noted the optimization may be performed iteratively in step 1404 until a desirable result is obtained.

In step 1405, the sub-images may be calibrated in accordance with the results of the registration in step 1403 or the fine registration in step 1405. The results may be one or more offsets including, for example, offsets in the X direction (X offsets), offsets in the Y direction (Y offsets), offsets in the Z direction (Z offsets), offsets in the coronal plane (coronal offsets), offsets in the sagittal plane (sagittal offsets), offsets in the transverse plane (transverse offset), etc. Afterwards the calibrated sub-images may be fused together to generate a composite image. Particularly, the overlapping images corresponding to 3D volume data representing the overlapping regions of the sub-images may be fused.

The composite image may be output for display in step 1406. In the exemplary context of angiography, a composite image of the vasculature including one or more blood vessels of a region of interest may be obtained for, for example, diagnosis purposes. It should be noted that, apart from vascular diseases, the method described in the disclosure may be utilized to diagnose a region of interest such as head, thorax, abdomen, pelvis and perineum, limbs, spine and vertebrae, or the like, or a combination thereof. Specifically, the head may include brain or skull, eye, teeth, or the like, or a combination thereof. The thorax may include cardiac, breast, or the like, or a combination thereof. The abdomen may include kidney, liver, or the like, or a combination thereof. The limbs may include an arm, a leg, a wing of a bird, or the like, or a combination thereof.

It should be noted that the flowchart described above is provided for the purposes of illustration, and may not intend to limit the scope of the present disclosure. For persons having ordinary skills in the art, various variations and modifications may be conducted under the guidance of the present disclosure. However, those variations and modifications do not depart the scope of the present disclosure. For example, the region of interest may be a gastrointestinal tract. Three or more overlapping images corresponding to 3D volume data may be registered in step 1403. Step 1404 may be unnecessary, and step 1403 may proceed to step 1405 directly.

Figure 15:
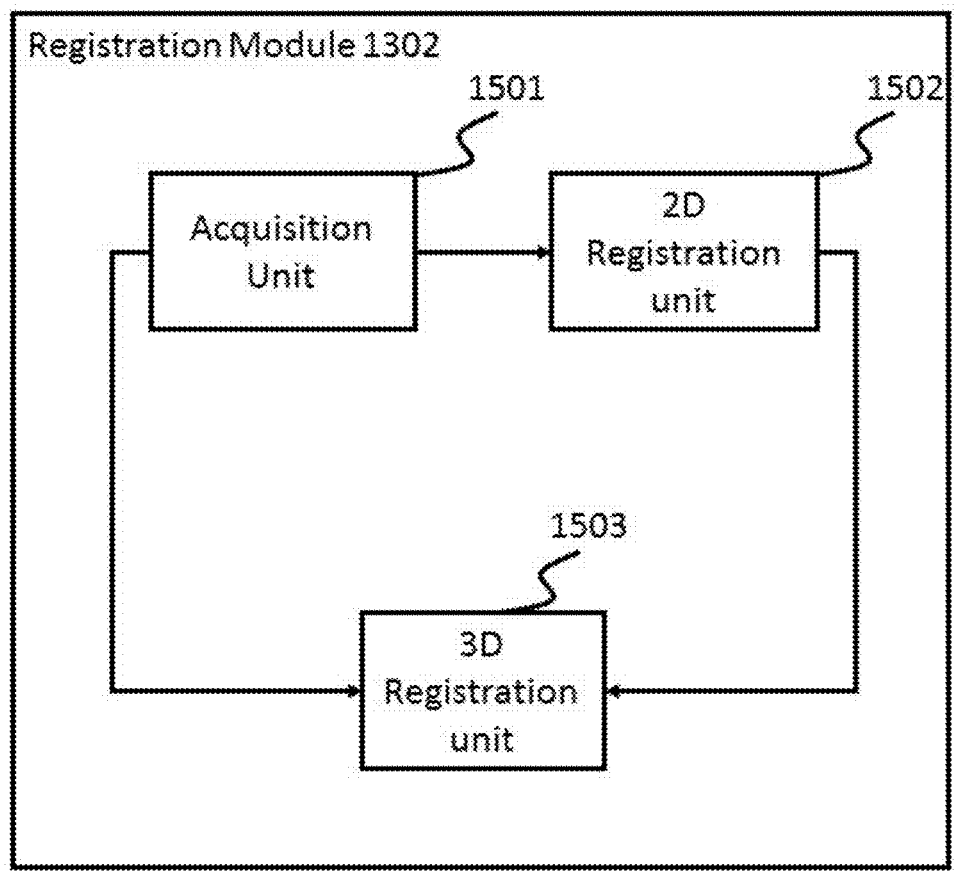
FIG. 15 is a block diagram illustrating a registration module according to some embodiments of the present disclosure.

FIG. 15 depicts a block diagram of the registration module 1302 according to some embodiments of the present disclosure. The registration module 1302 may include an acquisition unit 1501, a 2D registration unit 1502, and a 3D registration unit 1503. The acquisition unit 1501 may be configured to acquire images to be registered. The images may be 3D images, 2D images, or the like, or a combination thereof. Particularly, the 3D images may be 3D-DSA images. For instance, the 3D-DSA images may be 3D digital coronal images, 3D digital sagittal images, 3D digital transverse images, or the like, or a combination thereof. In some embodiments of the present disclosure, one or more overlapping images corresponding to 3D volume data of adjacent sub-images which have mutual overlapping regions may be acquired by the acquisition unit 1501. The overlapping images corresponding to 3D volume data may include a stack of 2D images.

A 2D registration may be performed by the 2D registration unit 1502. Overlapping images corresponding to 3D volume data may be projected onto a coronal plane, a sagittal plane, a transverse plane, etc. The projection may be based on maximum intensity projection (MIP). Optionally and preferably, the projection may be based on temporal maximum intensity projection (tMIP), minimum intensity projection (MiniP), virtual endoscopic display (VED), or the like, or a combination thereof. The following description is provided in the exemplary context of MIP. This is for illustration purposes only, and not intended to limit the scope of the present disclosure. Other types of projection may be used to generate a 2D projection map. By way of MIP, a 2D projection image and a pixel map may be generated based on a set of 3D volume data. An overlapping region may correspond to two sets of 3D volume data, one set relating to one of two adjacent 3D sub-images. By way of MIP, two 2D projection images and two corresponding pixel maps may be generated.

The 2D registration may include uncover the correlation between the 2D projection images. The correlation may be utilized to determine 2D offsets of the two corresponding pixel maps. The correlation or the 2D offsets may be used to calibrate the pixel maps. The calibration may be performed by the 2D registration unit 1502. Merely by way of example, the overlapping images corresponding to 3D volume data may have a stack of 2D images in the coronal plane. The overlapping images may be projected onto the coronal plane. Alternatively, the overlapping images corresponding to 3D volume data may be projected on another plane, for example, a self-defined plane. It should be noted that the 2D offsets may include offsets in different directions or different planes, for example, offsets in the X direction (X offsets), offsets in the Y direction (Y offsets), offsets in the Z direction (Z offsets), offsets in the coronal plane (coronal offsets), offsets in the sagittal plane (sagittal offsets), offsets in the transverse plane (transverse offset), etc.

The 3D registration unit 1503 may be configured to calculate 3D offsets and perform 3D registration on the overlapping images corresponding to 3D volume data based on the 2D offsets and the 3D offsets. It should be noted that the 3D offsets may include offsets in different directions or different planes, for example, offsets in the X direction (X offsets), offsets in the Y direction (Y offsets), offsets in the Z direction (Z offsets), offsets in the coronal plane (coronal offsets), offsets in the sagittal plane (sagittal offsets), offsets in the transverse plane (transverse offset), etc.

It should be understood that the preceding description of the registration module is merely provided for the purposes of illustration, and not intended to limit the scope of the present disclosure. For persons having ordinary skills in the art, various variations and modifications may be made in the light of the present disclosure. However, those variations and modifications do not depart from the protecting scope of the present disclosure. For example, the 3D registration may be performed on the overlapping images corresponding to 3D volume data directly without performing a 2D registration. As another example, the 2D registration may be solely performed without performing a 3D registration.

Figure 16:
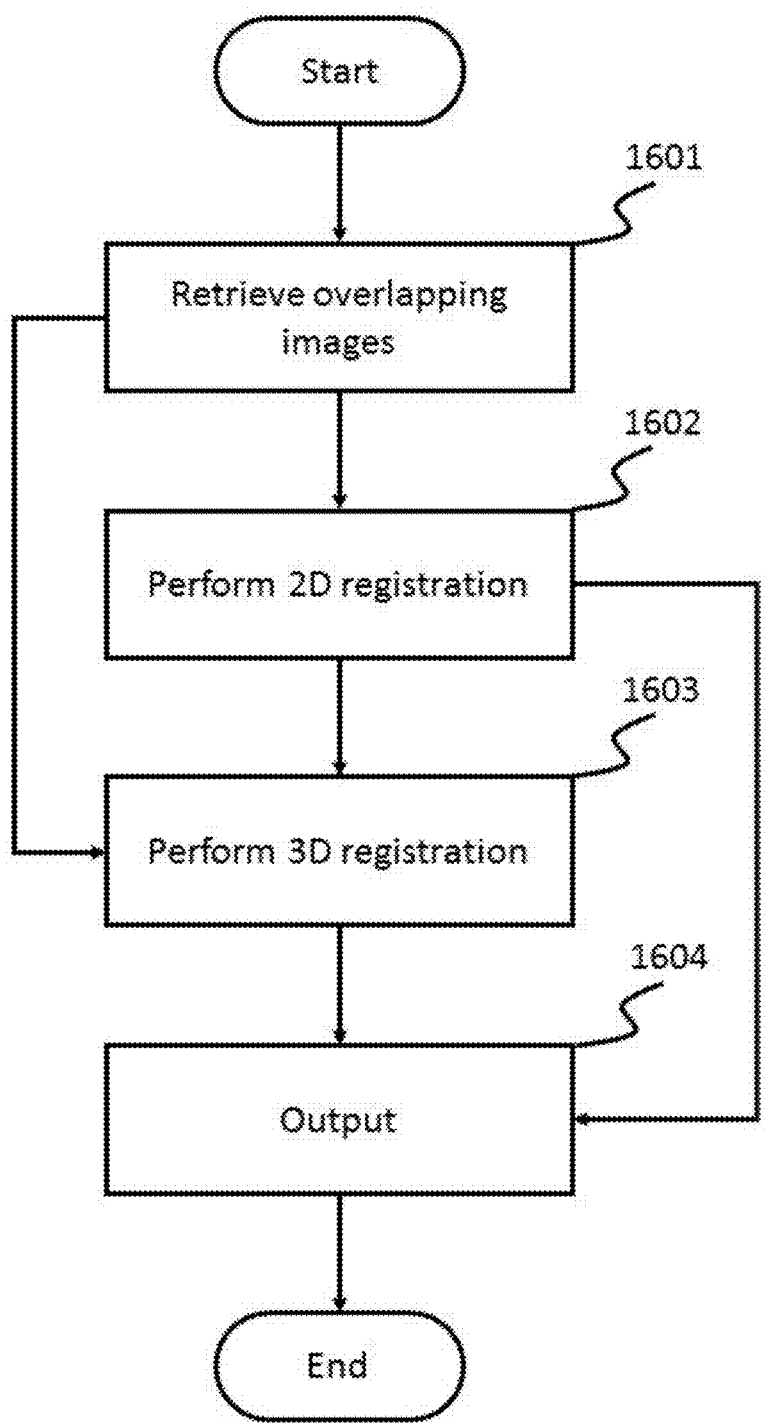
FIG. 16 is a flowchart illustrating a registration process according to some embodiments of the present disclosure.

FIG. 16 is a flowchart illustrating a registration process according to some embodiments of the present disclosure. Overlapping images corresponding to 3D volume data may be retrieved in step 1601. The overlapping images corresponding to 3D volume data may be generated by segmenting sub-images, which is described elsewhere in the present disclosure. The overlapping images corresponding to 3D volume data may include a stack of 2D images. Merely by way of example, the overlapping images corresponding to 3D volume data may be projected onto any plane of the anatomical planes. Exemplary anatomical plane may include a coronal plane, a sagittal plane, a transverse plane, etc. Specifically, when the overlapping images corresponding to 3D volume data include 3D digital coronal images, the overlapping images corresponding to 3D volume data may be projected onto the coronal plane. Likewise, when the overlapping images corresponding to 3D volume data include 3D digital sagittal images, the overlapping images corresponding to 3D volume data may be projected onto the sagittal plane. Two-dimensional projection images of the overlapping images corresponding to two sets of 3D volume data and the corresponding pixel maps may be generated after the projection is completed. The projection may be based on maximum intensity projection (MIP). Optionally and preferably, the projection may be based on temporal maximum intensity projection (tMIP), minimum intensity projection (MiniP), virtual endoscopic display (VED), or the like, or a combination thereof.

A 2D registration may be performed on the 2D images in step 1602. The 2D registration may include calculating 2D offsets and applying 2D offsets. It should be noted that the 2D offsets may include offsets in different directions or different planes, for example, offsets in the X direction (X offsets), offsets in the Y direction (Y offsets), offsets in the Z direction (Z offsets), offsets in the coronal plane (coronal offsets), offsets in the sagittal plane (sagittal offsets), offsets in the transverse plane (transverse offset), etc. Any number of 2D images of the overlapping images corresponding to 3D volume data may be registered in step 1602.

In step 1603, a 3D registration may be performed on the overlapping images corresponding to 3D volume data based on the 2D offsets and 3D offsets generated hereby. It should be noted that the 3D offsets may include offsets in different directions or different planes, for example, offsets in the X direction (X offsets), offsets in the Y direction (Y offsets), offsets in the Z direction (Z offsets), offsets in the coronal plane (coronal offsets), offsets in the sagittal plane (sagittal offsets), offsets in the transverse plane (transverse offset), etc. Specifically, the 3D offsets may be generated based on the 2D offsets in the plane onto which the overlapping images have been projected to generate the 2D projection images and the slice information of the overlapping images corresponding to 3D volume data. The slice information may indicate the slice number of a pixel of a 2D projection image. In step 1604, the overlapping images corresponding to 3D volume data may be output for further processing.

It should be noted that the flowchart described above is provided for the purposes of illustration, and not necessarily intended to limit the scope of the present disclosure. Apparently for persons having ordinary skills in the art, numerous variations and modifications may be conducted under the teaching of the present disclosure. However, those variations and modifications do not depart the protecting scope of the present disclosure. For example, the 3D registration may be performed directly on the overlapping images corresponding to 3D volume data without performing a 2D registration. As another example, the 2D registration may be performed solely on the overlapping images corresponding to 3D volume data without performing a 3D volume data.

Figure 17:
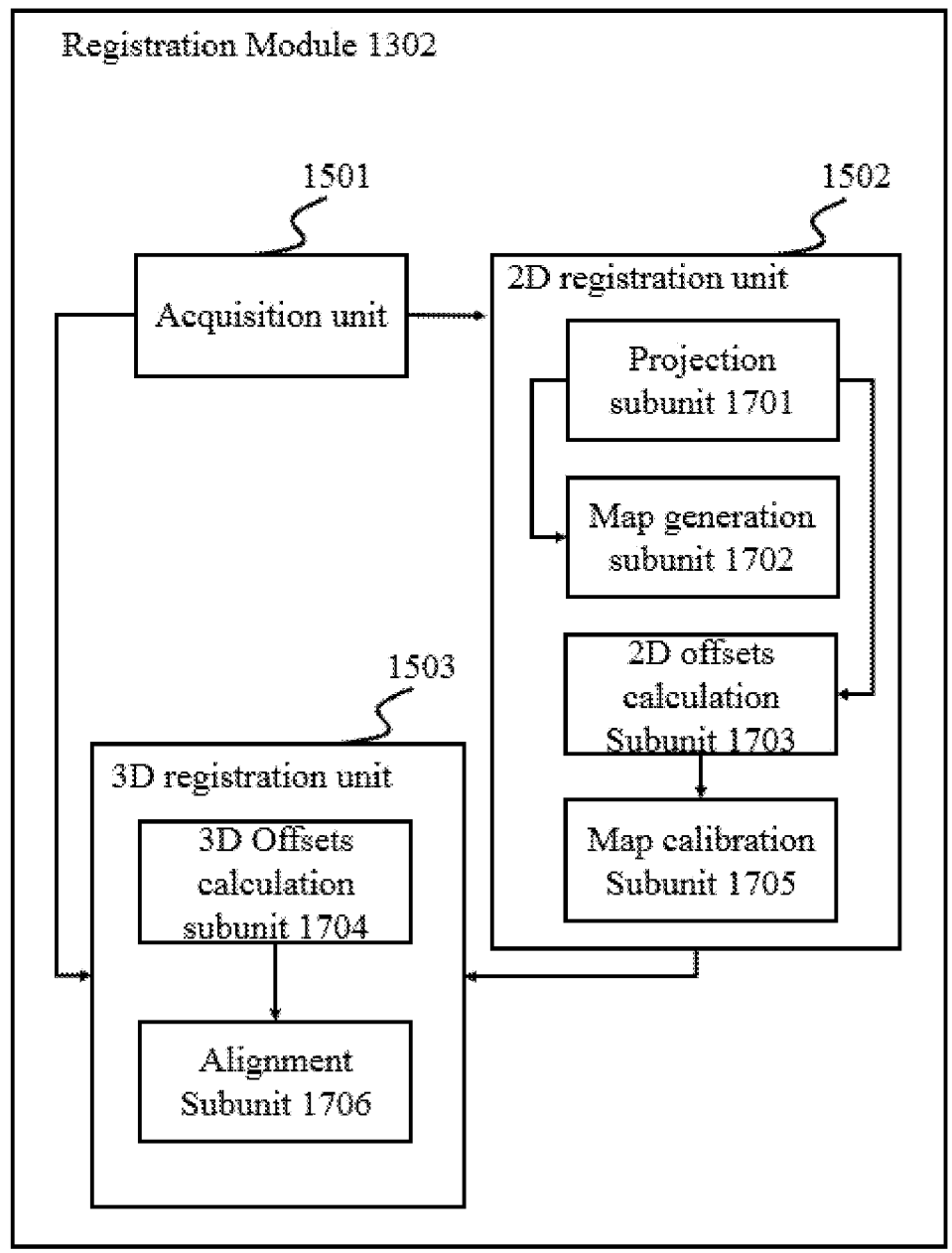
FIG. 17 is a block diagram of a registration module according to some embodiments of the present disclosure.

FIG. 17 is a block diagram of the registration module 1302 according to some embodiments of the present disclosure. The registration module 1302 may include an acquisition unit 1501, a 2D registration unit 1502, and a 3D registration unit 1503. The 2D registration unit may include a projection subunit 1701, a map generation subunit 1702, a 2D offsets calculation subunit 1703, and a map calibration subunit 1705. The 3D registration unit may include a 3D offsets calculation subunit 1704 and an alignment subunit 1706. The acquisition unit 1501 may be configured to acquire images to be registered. The images may be 3D images, 2D images, or the like, or a combination thereof. Particularly, the 3D images may be 3D-DSA images. Optionally and preferably the 3D-DSA images may be 3D digital coronal images, 3D digital sagittal images, 3D digital transverse images, or the like, or a combination thereof.

In some embodiments of the present disclosure, one or more overlapping images corresponding to 3D volume data of adjacent sub-images that have overlapping regions may be acquired by the acquisition unit 1501. A 2D registration may be performed on 2D projection images generated by projecting the overlapping images corresponding to 3D volume data on an anatomical plane. Exemplary anatomical planes may include a coronal plane, a sagittal plane, a transverse plane, etc. Alternatively, the overlapping images corresponding to 3D volume data may be projected on any plane, for example, a self-defined plane. The 2D registration may be performed by the 2D registration unit 1502. The projection subunit 1701 may be configured to perform the projection. The projection may be based on maximum intensity projection (MIP). Optionally and preferably, the projection may be based on temporal maximum intensity projection (tMIP), minimum intensity projection (MiniP), virtual endoscopic display (VED), or the like, or a combination thereof.

The map generation subunit 1702 may be configured to generated pixel maps of the 2D projection images based on the 2D projection images generated by the projection subunit 1701. The 2D projection images and the pixel maps may be generated simultaneously. In alternative embodiments, the 2D projection images and the pixel maps may be generated sequentially at any order. The 2D offsets calculation subunit 1703 may be configured to generate 2D offsets based on the 2D projection images. It should be noted that the 2D offsets may include offsets in different directions or different planes, for example, offsets in the X direction (X offsets), offsets in the Y direction (Y offsets), offsets in the Z direction (Z offsets), offsets in the coronal plane (coronal offsets), offsets in the sagittal plane (sagittal offsets), offsets in the transverse plane (transverse offset), etc.

In some embodiments of the present disclosure, the map generation subunit 1702 may generate one or more pixel maps of the overlapping images corresponding to 3D volume data. The pixel maps may correspond to the 2D projection images generated by the 2D registration unit 1502. Merely by way of example, when an overlapping image corresponding to 3D volume data is projected onto the coronal plane, a pixel map on the coronal plane may be generated. When a LPS coordinate system as described in FIG. 7 is employed, the X-Z plane may indicate the coronal plane, and the overlapping images corresponding to 3D volume data may be projected onto the X-Z plane. A pixel value of the pixel map may be the slice number corresponding to a slice of an overlapping image corresponding to 3D volume data that has the maximum intensity at a pixel (x, z). For example, an overlapping image corresponding to 3D volume data may have 80 slices. When the overlapping image corresponding to 3D volume data is projected onto an anatomical plane (e.g., a coronal plane, a sagittal plane, a transverse plane) to generate a 2D projection image, each pixel of the 2D projection image may correspond to 80 pixels at the same (x, z) distributed among 80 slices of the overlapping image corresponding to 3D volume data. The pixel value of the pixel map corresponding to the 2D image may be the slice number corresponding to a slice that has the maximum intensity at the pixel (x, z) among the 80 slices. Specifically, if the $55^{th}$ slice of the overlapping image corresponding to 3D volume data has the maximum intensity at the pixel (xi, zi), then the pixel value corresponding to the 2D image at pixel (xi, zi) that is the projection of the overlapping image corresponding to 3D volume data may be assigned to 55.

The 3D offsets calculation subunit 1704 may be configured to calculate 3D offsets. The calculation may be based on the pixel maps. The pixel map generated by the map generation subunit 1702 may be calibrated by the map calibration subunit 1705. The calculation may be based on the 2D offsets. A calibrated pixel map may be generated after the calibration is completed. In alternative embodiments of the present disclosure, no calibration is performed on the pixel maps. In some embodiments, the 3D offsets may be obtained based on the 2D offsets. In alternative embodiments, the 3D offsets may be obtained based on the pixel maps, for example, two pixel maps, or a pixel map and a calibrated pixel map. Merely by way of example, one of the two pixel maps may be designated as a reference pixel map, and the other may be designated as the floating pixel map. The 3D offsets may be calculated through a comparison of the pixel values of corresponding pixels in the reference pixel map and in the floating pixel map. Furthermore, the 3D offsets may be calculated on the basis of probability distribution of the difference. The alignment subunit 1706 may be configured to perform 3D registration on the overlapping images corresponding to 3D volume data based on the 2D offsets and the 3D offsets.

It should be noted that the flowchart described above is provided for the purposes of illustration, and not necessarily intend to limit the scope of the present disclosure. Apparently for persons having ordinary skills in the art, numerous variations and modifications may be conducted under the teaching of the present disclosure. However, those variations and modifications do not depart from the protecting scope of the present disclosure. For example, the 2D offsets may not necessarily be utilized to calibrate a pixel map.

Figure 18:
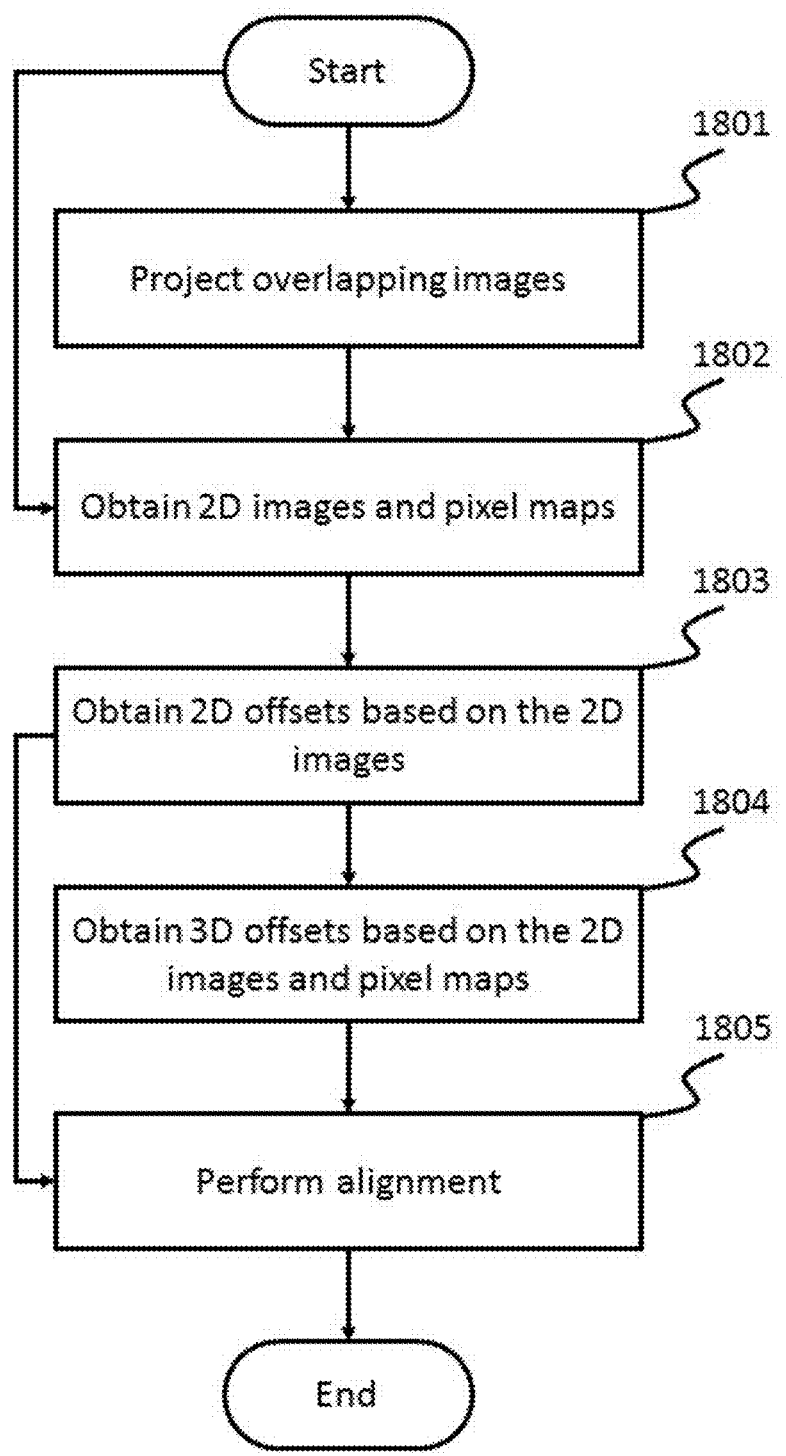
FIG. 18 is a flowchart illustrating a process of image registration according to some embodiments of the present disclosure.

FIG. 18 is a flowchart illustrating a process of image registration according to some embodiments of the present disclosure. Overlapping images corresponding to 3D volume data may be projected on any plane of the anatomical plane in step 1801. The anatomical plane may include a coronal plane, a sagittal plane, a transverse plane, etc. The projection may be based on maximum intensity projection (MIP). Optionally and preferably, the projection may be based on temporal maximum intensity projection (tMIP), minimum intensity projection (MiniP), virtual endoscopic display (VED), or the like, or a combination thereof.

In step 1802, 2D projection images of the overlapping images corresponding to 3D volume data and corresponding pixel maps may be obtained based on the projection performed in step 1801. The 2D projection images may correlate with the overlapping images corresponding to 3D volume data, as well as the pixel maps. A pixel value at a pixel (x, z) of the 2D projection images may be the maximum intensity of a corresponding pixel (x, z) of the slice among multiple slices of the overlapping image corresponding to 3D volume data. Two-dimensional offsets may be obtained based on the 2D projection images in step 1803. It should be noted that the 2D offsets may include offsets in different directions or different planes, for example, offsets in the X direction (X offset), offsets in the Y direction (Y offset), offsets in the Z direction (Z offset), offsets in the coronal plane (coronal offsets), offsets in the sagittal plane (sagittal offsets), offsets in the transverse plane (transverse offset), etc. The 2D offsets may be utilized to perform further registration, e.g., 3D registration, a pixel map calibration.

In some embodiments, the pixel maps may be calibrated in step 1804. The calibration may be based on the 2D offsets. 3D offsets may be obtained based on the 2D offsets and the pixel maps in step 1804. In some embodiments, the 3D offsets may be obtained based on the 2D offsets. In alternative embodiments, the 3D offsets may be obtained based on the pixel maps, for example, two pixel maps, or a pixel map and a calibrated pixel map. In step 1805, the alignment may be performed to register the overlapping images corresponding to 3D volume data based on the 2D offsets and the 3D offsets.

It should be noted that the flowchart described above is provided for the purposes of illustration, and not necessarily intend to limit the scope of the present disclosure. Apparently for persons having ordinary skills in the art, numerous variations and modifications may be conducted under the teaching of the present disclosure. However, those variations and modifications do not depart from the protecting scope of the present disclosure. For example, step 1803 may proceed to step 1805 directly without performing step 1804.

Figure 19:
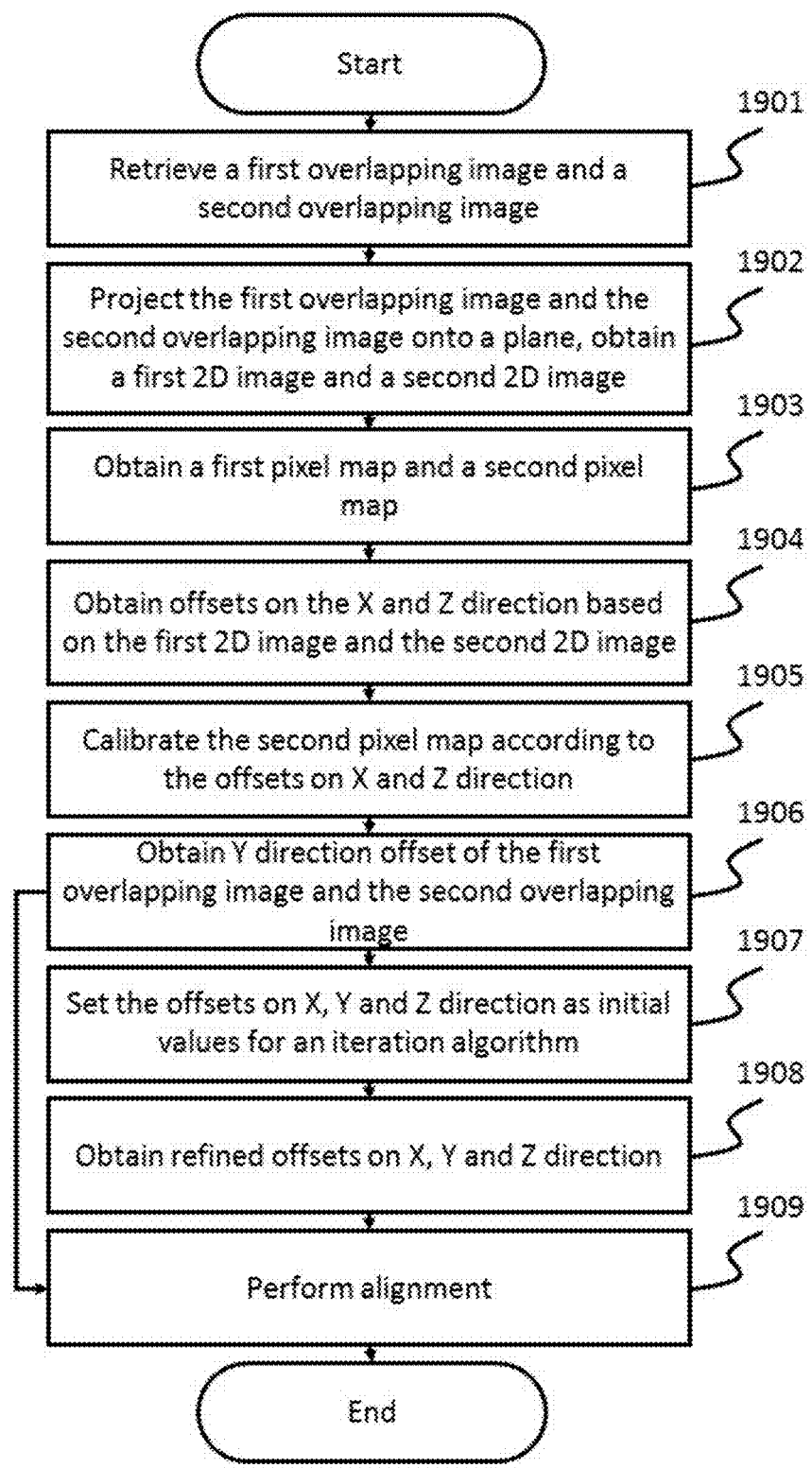
FIG. 19 is a flowchart illustrating a process of image registration according to some embodiments of the present disclosure.

FIG. 19 is a flowchart illustrating a process of image registration according to some embodiments of the present disclosure. As described in FIG. 7, a LPS coordinate system may be employed herein. As shown in FIG. 7, the X-Y-Z axis defines a three dimensional space such that the origin of it locates within the chest of a target body. In step 1901, a first overlapping image correspond to 3D volume data and a second overlapping image corresponding to 3D volume data may be retrieved. The two overlapping images may represent an overlapping region of two sub-images, the sub-images may be combined to generate a composite image. The overlapping images corresponding to 3D volume data may be segmented from the sub-images by the segmentation module 1301 that is described elsewhere in the present disclosure.

In step 1902, the first overlapping image correspond to 3D volume data and the second overlapping image correspond to 3D volume data may be projected onto an anatomical plane. The anatomical plane may include a coronal plane, a sagittal plane, a transverse plane, etc. The projection may be based on maximum intensity projection (MIP). Optionally and preferably, the projection may be based on temporal maximum intensity projection (tMIP), minimum intensity projection (MiniP), virtual endoscopic display (VED), or the like, or a combination thereof. A first 2D projection image corresponding to the first overlapping image and a second 2D projection image corresponding to the second overlapping image may be generated in step 1902 based on the projection. In some embodiments of the present disclosure, a pixel (x, z) of a 2D projection image may be assigned with the maximum intensity of corresponding pixels (x, z) of multiple slices constituting a 3D image. For instance, an overlapping image corresponding to 3D volume data may have 80 slices. The value of a pixel (x, z) of the 2D projection image may equal to the maximum intensity at the corresponding pixel (x, z) among the 80 slices.

In step 1903, a first pixel map correspond to the first 2D projection image and a second pixel map corresponding to the second 2D projection image may be generated. According to the description of the pixel map described elsewhere in the disclosure, a pixel value of the pixel map may be the slice number corresponding to a slice that has the maximum intensity among multiple slices of an overlapping image corresponding to 3D volume data.

In step 1904, the 2D projection images obtained in 1902 may be utilized to calculate 2D offsets. It should be noted that the 2D offsets may include offsets in different directions or different planes, for example, offsets in the X direction (X offset), offsets in the Y direction (Y offset), offsets in the Z direction (Z offset), offsets in the coronal plane (coronal offsets), offsets in the sagittal plane (sagittal offsets), offsets in the transverse plane (transverse offset), etc. In some embodiments, a Cartesian coordinate system may be employed herein. In some embodiments, the LPS coordinate system may be employed herein. The overlapping images corresponding to 3D volume data may be projected onto the X-Z plane corresponding to the coronal plane under an MIP. Therefore, the obtained 2D projection images are on the X-Y plane. In step 1904, an X offset and a Z offset may be obtained based on the first 2D projection image and the second 2D projection image. In step 1905, the X offset and the Z offset may be utilized to calibrate the second pixel map as described in step 1903. A calibrated pixel map may be generated from the calibration. In step 1906, a Y offset may be obtained by comparing the first pixel map and the calibrated pixel map. In some embodiments of the present disclosure, the comparison may be performed by way of a subtraction for corresponding pixels on the first pixel map and the calibrated pixel map (or on the reference pixel map and the floating pixel map). The probability or frequency of the differences obtained from the comparison may be assessed to provide a difference range. For example, if differences between 15 and 17 occur most, the difference range may be set to be 15-17. After the difference range is determined, an average value relating to all the pixel values of the first pixel map and the calibrated pixel map that are within the difference range may be calculated. The calculated average value may be determined as the Y offset. In some embodiments, the first pixel map and the second pixel map are compared to determine the Y offset when the correlation between the first pixel map and the second pixel map is determined. The correlation may be represented by the X offset and the Z offset between the first pixel map and the second pixel map.

In step 1907, the X offset, the Y offset, and the Z offset may be optimized in a fine registration by utilizing one or more algorithms. Exemplary algorithms may include recursion, a bisection method, an exhaustive method, a greedy algorithm, a divide and conquer algorithm, dynamic programming method, an iterative method, a branch-and-bound algorithm, a backtracking algorithm, or the like, or any combination thereof. The fine registration may be based on the 2D registration and/or 3D registration. In step 1908, an optimized X offset, an optimized Y offset, and an optimized Z offset may be generated. In step 1909, an alignment may be performed to register the overlapping images corresponding to 3D volume data based on the X offset, the Y offset, and the Z offset, or the optimized offsets.

It should be understood that the description of the flowchart above is merely provided for the purposes of illustration, and not intended to limit the scope of the present disclosure. For persons having ordinary skills in the art, numerous variations and modifications may be made under the teaching of the present disclosure. However, those variations and modifications do not depart from the protecting scope of the present discourse. For instance, step 1902 and step 1903 may be performed concurrently, or sequentially at any order. The calibration in step 1905 may be performed on the first pixel instead of the second pixel map. The Y offset obtained in step 1906, together with the X offset and the Z offset obtained in step 1905, may be utilized directly to perform the 3D registration without performing step 1907 and step 1908.

Figure 20:
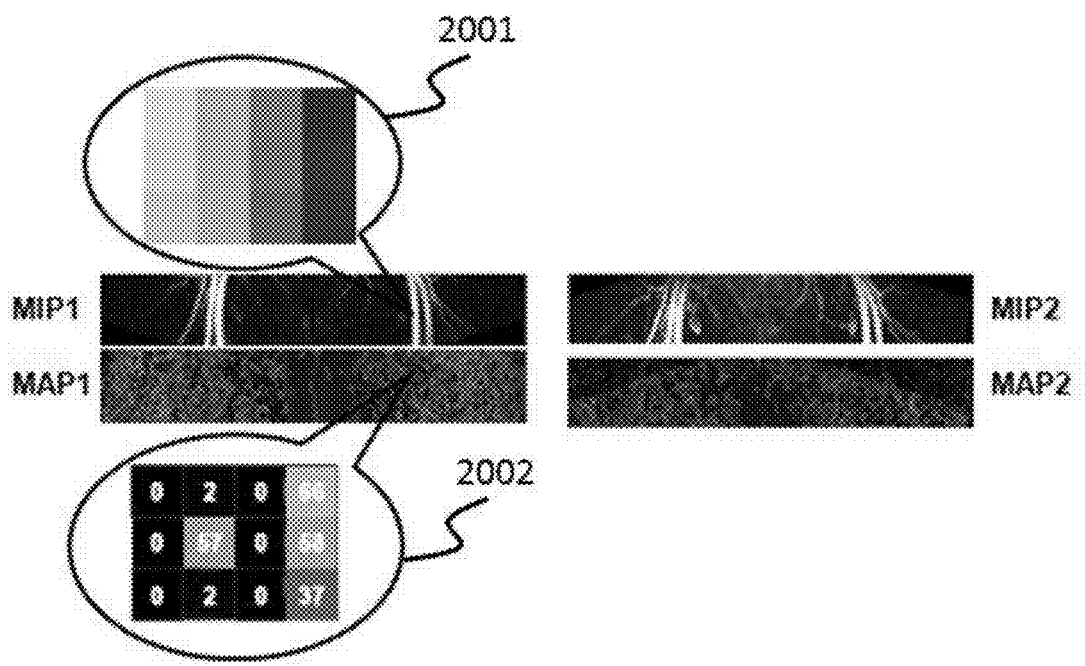
FIG. 20 illustrates 2D images and corresponding pixel maps according to some embodiments of the present disclosure.

FIG. 20 illustrates 2D images and corresponding pixel maps generated by MIP according to some embodiments of the present disclosure. As shown in the figure, two overlapping images corresponding to 3D volume data may be projected onto the coronal plane, as a result, 2D projection images MIP1 and MIP2 may be generated. As the overlapping images corresponding to 3D volume data is projected onto the coronal plane, two pixel maps corresponding to MIP1 and MIP2 respectively may be generated along with the 2D projection images. As illustrated in the figure, MAP1 is a pixel map corresponding to the 2D projection image MIP1, while MAP2 is another pixel map corresponding to the 2D projection image MIP2. The pixel values of MAP1, as well as MAP2, may correlate with those of MIP and MIP2 respectively. Region 2001 is a partial zoom of the 2D projection image MIP1. By way of MIP, every pixel of MIP1 may have a value of the maximum intensity corresponding to multiple slices of the overlapping image corresponding to 3D volume. Region 2002 is a partial zoom of the pixel map MAP1. Every pixel value of MAP1 may be a slice number of a slice with the maximum intensity, for example, grey value. For instance, as shown in region 2002, number 57 may indicate that the 57$^{th}$ slice of the corresponding overlapping image corresponding to 3D volume data has the maximum intensity. Thus the number 57 is stored in corresponding pixel of MAP1.

It should be understood that the 2D images and the corresponding pixel maps described above are provided for the purposes of illustration, and are not meant to limit the scope of the present disclosure. Apparently for persons having ordinary skills in the art, multiple variations and modifications may be made under the teaching of the disclosure. However, those variations and modifications do not depart from the spirit of the present closure.

Figure 21:
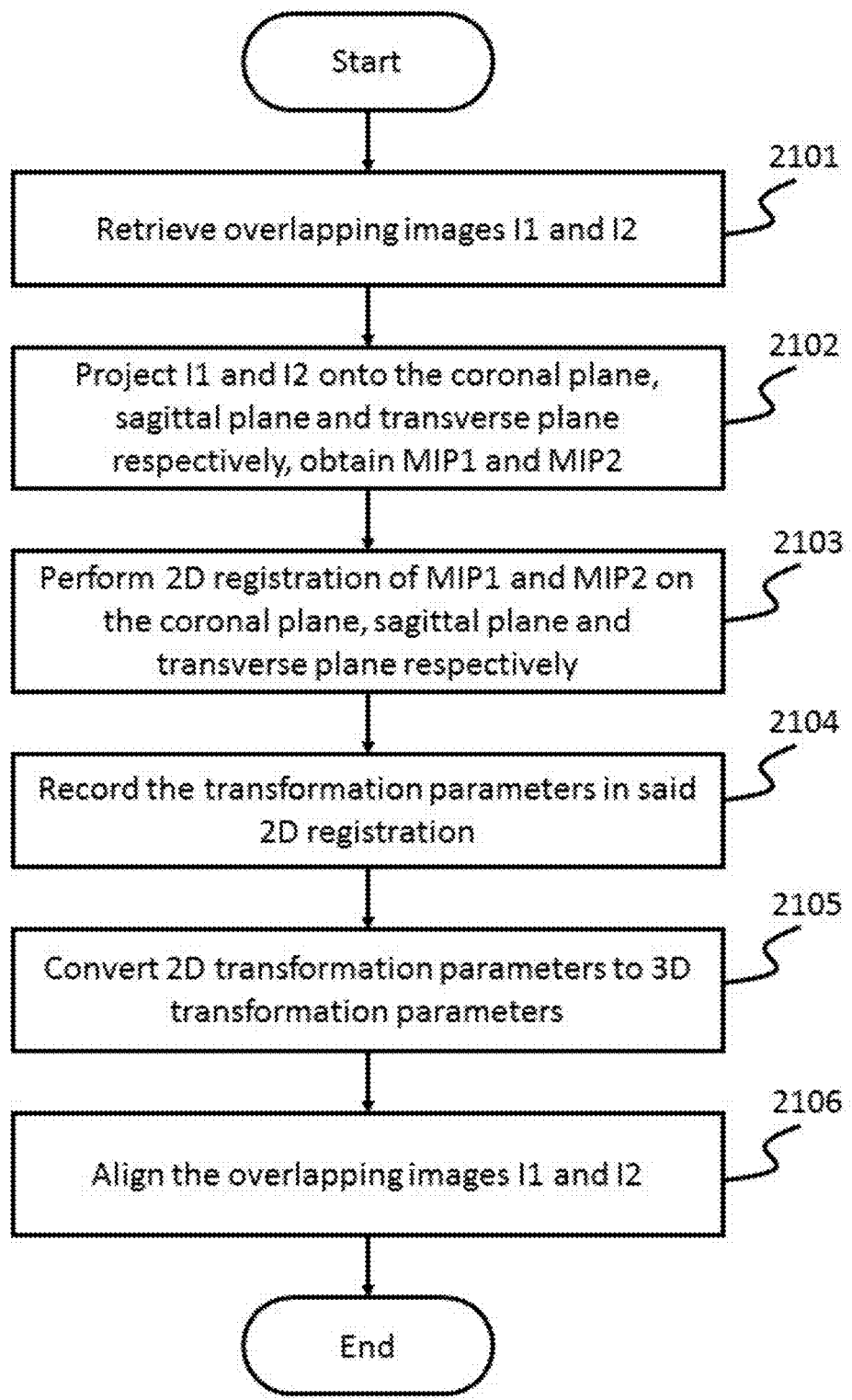
FIG. 21 is a flowchart illustrating a process of image registration according to some embodiments of the present disclosure.

FIG. 21 is a flowchart illustrating a process of image registration according to some embodiments of the present disclosure. In step 2101, two overlapping images corresponding to 3D volume data I1 and I2, may be retrieved. Both I1 and I2 may be overlapping regions of two sub-images and segmented from the sub-images by the segmentation module 1301 as described elsewhere in the disclosure. The overlapping images corresponding to 3D volume data may be obtained through techniques including DSA (digital subtraction angiography), CT (computed tomography), CTA (computed tomography angiography), PET (positron emission tomography), X-ray, MRI (magnetic resonance imaging), MRA (magnetic resonance angiography), SPECT (single-photon emission computerized tomography), US (ultrasound scanning), or the like, or a combination thereof. As an example employing MRA, the overlapping images corresponding to 3D volume data may be obtained by performing a segmentation in accordance with DICOM (digital imaging and communication in medicine). Particularly, label (0020 0032) of DICOM may be utilized to segment overlapping images corresponding to 3D volume data out of the sub-images.

In step 2102, the overlapping images corresponding to 3D volume data may be projected onto an anatomical plane. The anatomical plane may include a coronal plane, a sagittal plane, a transverse plane, etc. The projection may be based on maximum intensity projection (MIP). Optionally and preferably, the projection may be based on temporal maximum intensity projection (tMIP), minimum intensity projection (MiniP), virtual endoscopic display (VED), or the like, or a combination thereof. In some embodiments of the present disclosure, I1 and I2 may be projected onto the coronal plane, the sagittal plane, and the transverse plane respectively by performing an MIP. Thus, in every anatomical plane, two 2D projection images corresponding to I1 and I2, MIP1 and MIP2 are acquired. In step 2103, a 2D registration may be performed on MIP1 and MIP2 in each anatomical plane.

In step 2104, as the result of the 2D registration in step 2203, three groups of transformation parameters, (T$_{COR\_X}$, T$_{COR\_Z}$), (T$_{SAG\_Y}$, T$_{SAG\_Z}$), (T$_{AXI\_X}$, T$_{AXI\_Y}$), may be generated. In step 2105, the transformation parameters generated in step 2104 may be utilized to generate 3D transformation parameters in accordance with the following equations:

$$a.\ t_x = \frac{T_{COR\_X} + T_{AXI\_X}}{2} \quad (029)$$

$$b.\ t_y = \frac{T_{SAG\_Y} + T_{AXI\_Y}}{2} \quad (030)$$

$$c.\ t_z = \frac{T_{COR\_Z} + T_{SAG\_Z}}{2} \quad (031)$$

In step 2106, an alignment may be performed on the overlapping images corresponding to 3D volume data for a 3D registration based on the 3D transformation parameter $(t_x, t_y, t_z)$.

It should be understood that the flowchart described above is merely provided for the purposes of illustration, and not intended to limit the scope of the present disclosure. For persons having ordinary skills in the art, numerous variations and modifications may be made under the teaching of the present disclosure. However, those variations and modifications do not depart from the protecting scope of the present discourse.

Figure 22:
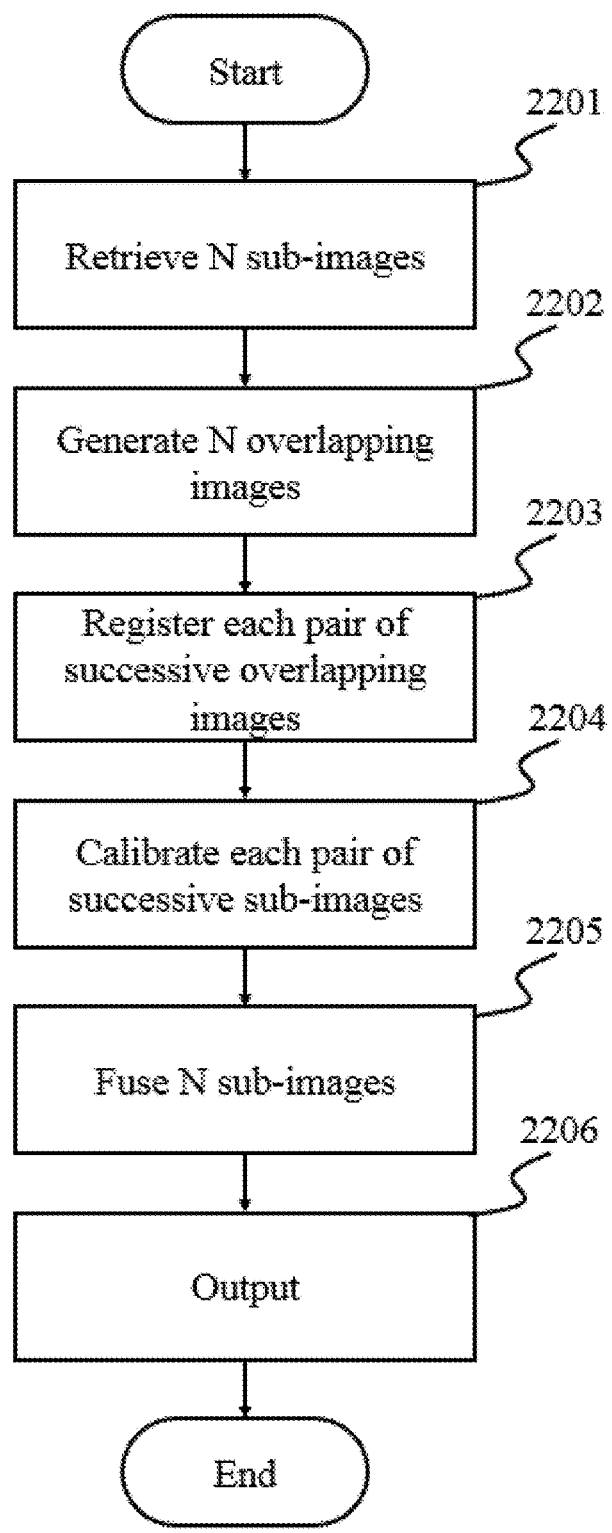
FIG. 22 is a flowchart illustrating a process of N sub-images registration according to some embodiments of the present disclosure.
Figure 23A:
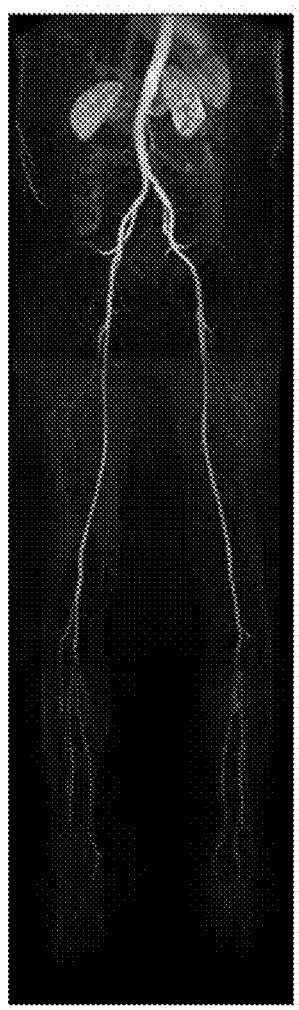
FIGS. 23A-23I illustrate exemplary 2D images of blood vessels according to some embodiments of the present disclosure.
Figure 23B:
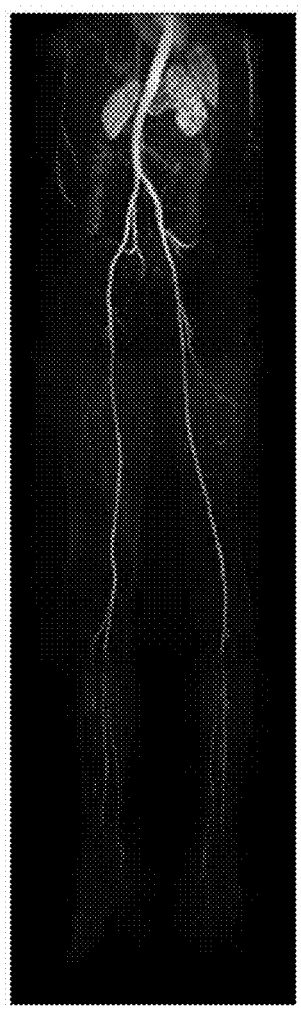
Figure 23C:
Figure 23D:
Figure 23E:
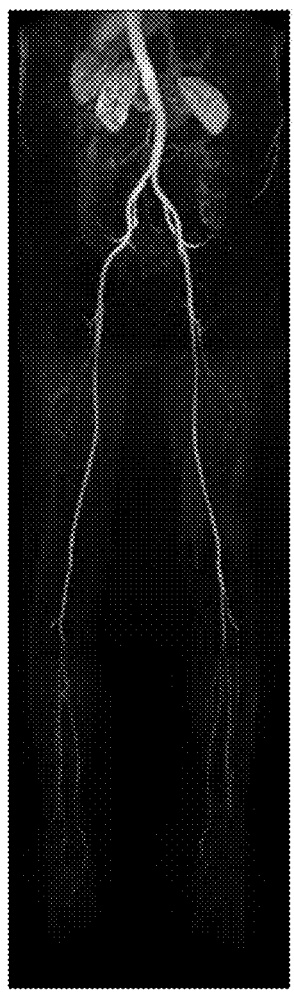
Figure 23F:
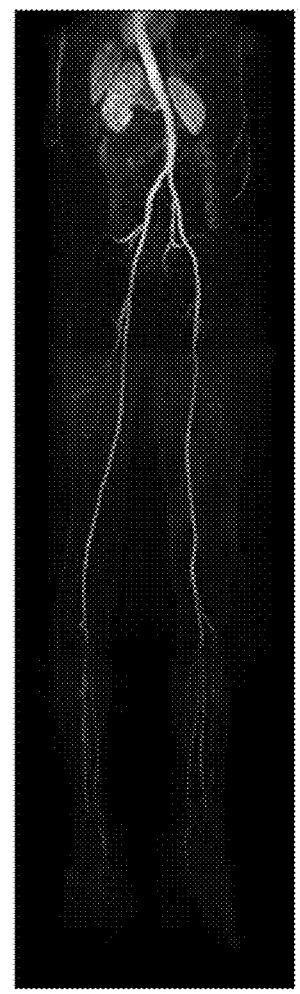
Figure 23G:
Figure 23H:
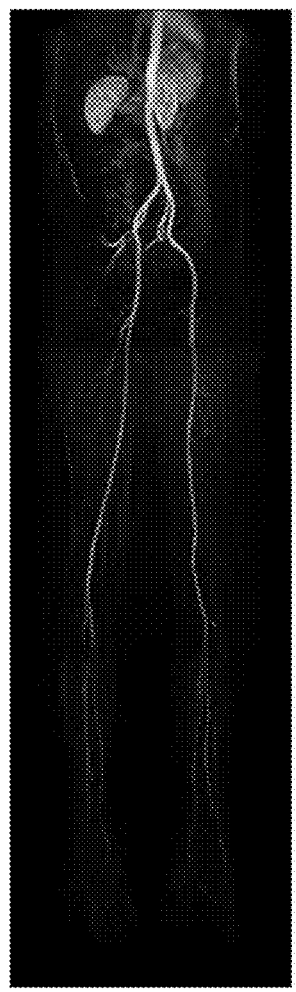
Figure 23I:
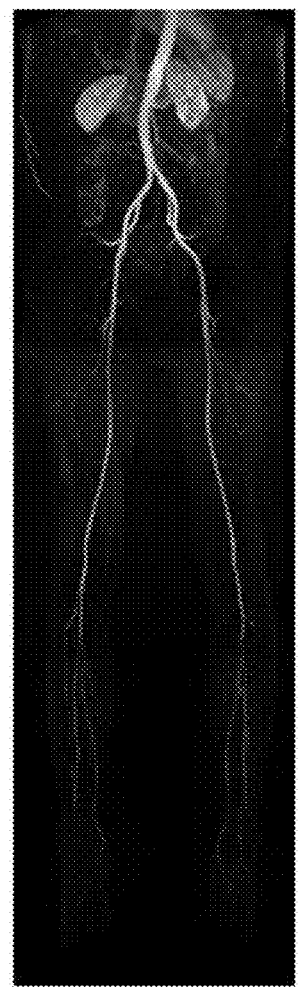

FIG. 22 is a flowchart illustrating a process of N sub-images registration according to some embodiments of the present disclosure. In step 2201, N sub-images of a series of scans may be retrieved, and each two successive sub-images may have one or more overlapping regions. In step 2202, each sub-image may be segmented by the segmentation module 1301 to produce an overlapping image corresponding to 3D volume data that represents the overlapping region. In step 2203, one or more registrations may be performed on each pair of successive overlapping images corresponding to 3D volume data, and 2D offsets and/or 3D offsets may be generated. It should be noted that the 2D offsets, or the 3D offsets, may include offsets in different directions or different planes, for example, offsets in the X direction, offsets in the Y direction, offsets in the Z direction, offsets in the coronal plane (coronal offsets), offsets in the sagittal plane (sagittal offsets), offsets in the transverse plane (transverse offset), etc. The registrations may include 2D registration, 3D registration, or the like, or a combination thereof. The registrations of the overlapping images corresponding to 3D volume data are described elsewhere in the disclosure. In step 2204, each pair of successive sub-images may be calibrated in accordance with the results of the registration in step 2203. In step 2205, the calibrated sub-images may be fused to generate a composite image that may be used for disease diagnosis. Particularly, the overlapping images corresponding to 3D volume data representing the overlapping regions of the sub-images may be fused.

It should be understood that the flowchart described above is merely provided for the purposes of illustration, and not intend to limit the scope of the present disclosure. For persons having ordinary skills in the art, numerous variations and modifications may be made under the teaching of the present disclosure. However, those variations and modifications do not depart from the protecting scope of the present discourse.

EXAMPLES

FIGS. 23A-23I illustrate 9 exemplary 2D images of blood vessels obtained based on the system and process according to some embodiments of the present disclosure. Each 3D image was generated by combining three coronal sub-images as shown in the figure. Each sub-image had a size of 384*512*88. According to the label (0020 0032) that is specified in DICOM, the size of the maximum overlapping region of two successive sub-images was 384*72*88. The time for processing the sub-images according to the method provided in the disclosure was approximately 2.075 s. The hardware configuration was, Intel i5-2400 processor, 3.10 Ghz, 4 GB ROM (read-only memory), and 64-bit OS (operating system).

FIGS. 23A-23I are 9 2D vascular images in the coronal plane of a region of interest from different view angles ranging from 0° to 360°. An MIP was obtained based on the 3D sub-images. The 2D vascular images as illustrated were generated from a counter clockwise rotation on the composite 3D image. The rotation angle of FIG. 23A, FIG. 23B, FIG. 23C, FIG. 23D, FIG. 23E, FIG. 23F, FIG. 23G, FIG. 23H, FIG. 23I were 0°, 45°, 90°, 135°, 180°, 225°, 270°, 315°, 360°, respectively.

Figure 24A:
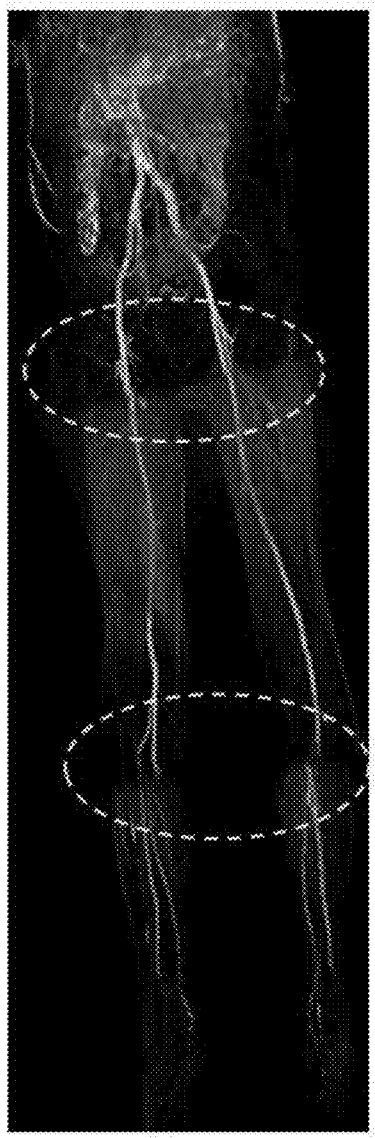
FIGS. 24A-24D illustrate 2D coronal images of vascular vessels applying different methods according to some embodiments of the present disclosure.
Figure 24B:
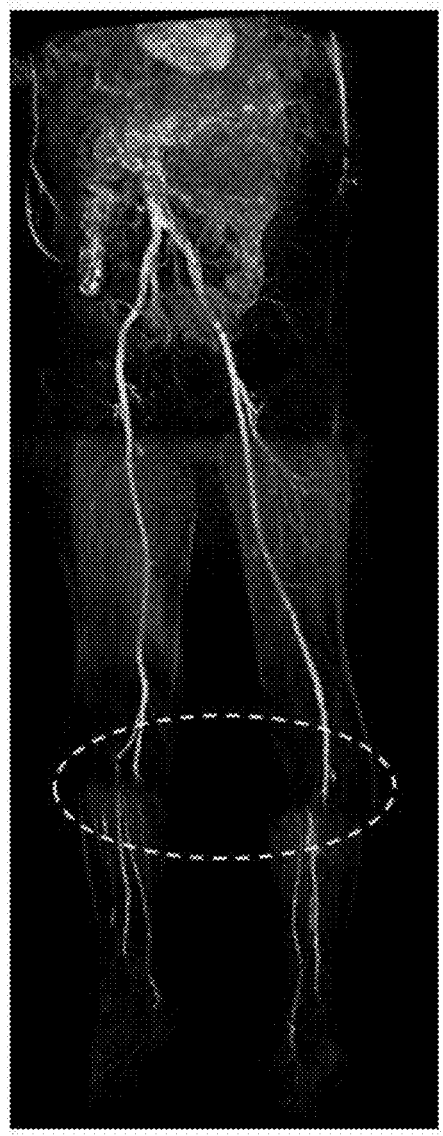
Figure 24C:
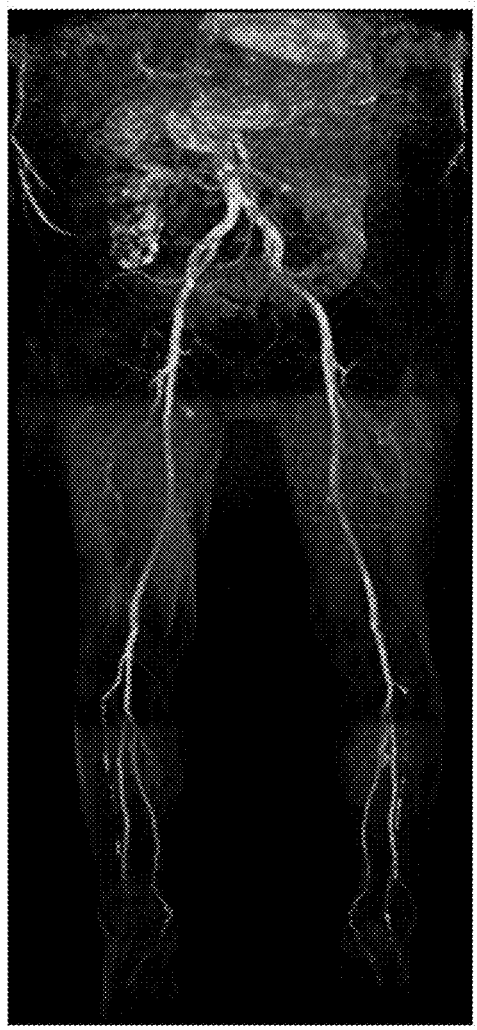
Figure 24D:

FIGS. 24A-24D illustrate four 2D coronal images of a region of interest depicting vasculature including a plurality of blood vessels. As shown in the figures, each 2D image was generated by combining three sub-images. FIG. 24A illustrates a 2D image that was generated without registration. FIG. 24B illustrates a 2D image that was generated based solely on 3D registration. FIG. 24C and FIG. 24D are 2D images of different view angles that were generated based on 2D and 3D registration by utilizing the system and process according to some embodiments of the present disclosure.

Figure 25A:
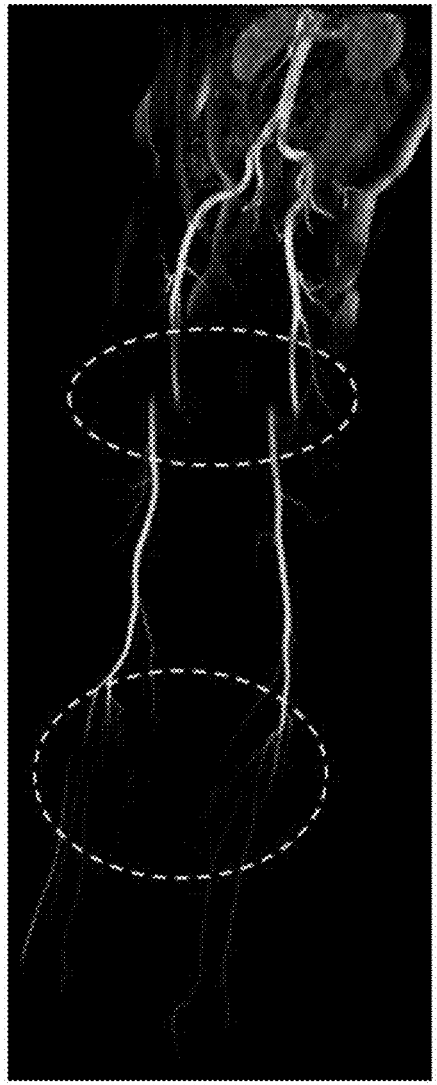
FIGS. 25A-25D illustrate 2D coronal images of vascular vessels applying different methods according to some embodiments of the present disclosure.
Figure 25B:
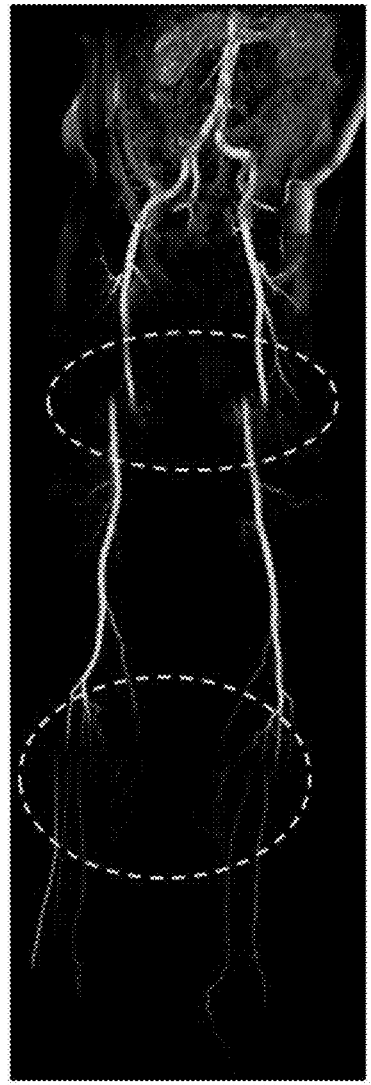
Figure 25C:
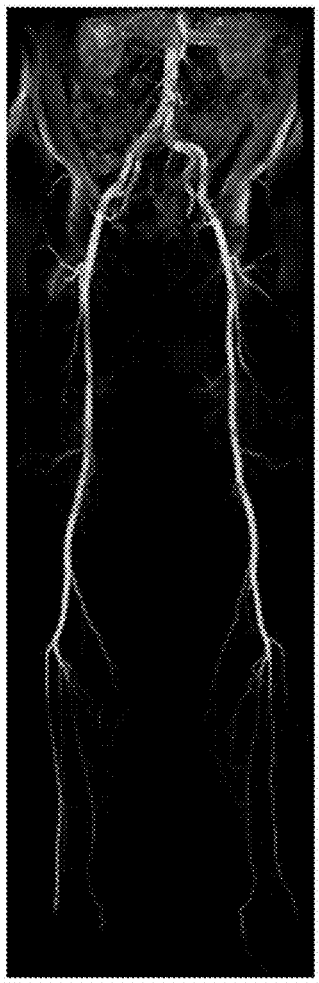
Figure 25D:

FIGS. 25A-25D illustrate 4 2D coronal images of a region of interest depicting vasculature including a plurality of blood vessels. As shown in the figure, each 2D image was generated by combining three sub-images. FIG. 25A illustrates a 2D image that was generated without registration. FIG. 25B illustrates a 2D image that was generated based solely on 3D registration. FIG. 25C and FIG. 25D are 2D images of different view angles that were generated based on 2D and 3D registration by utilizing the system and process according to some embodiments of the present disclosure.

Figure 26A:
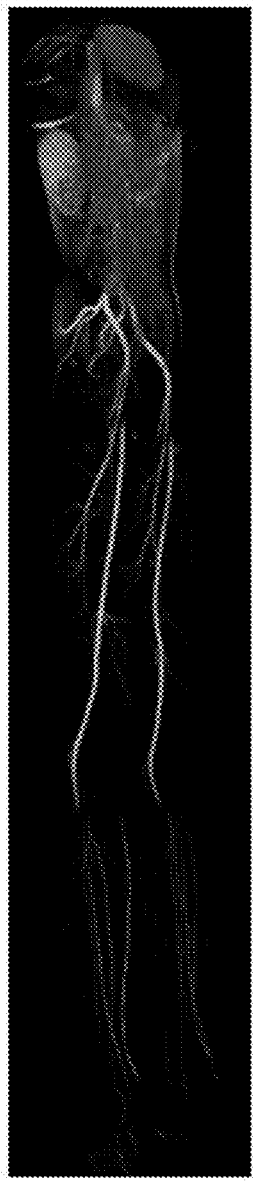
FIGS. 26A-26D illustrate 2D coronal images of vascular vessels applying different methods according to some embodiments of the present disclosure.
Figure 26B:
Figure 26C:
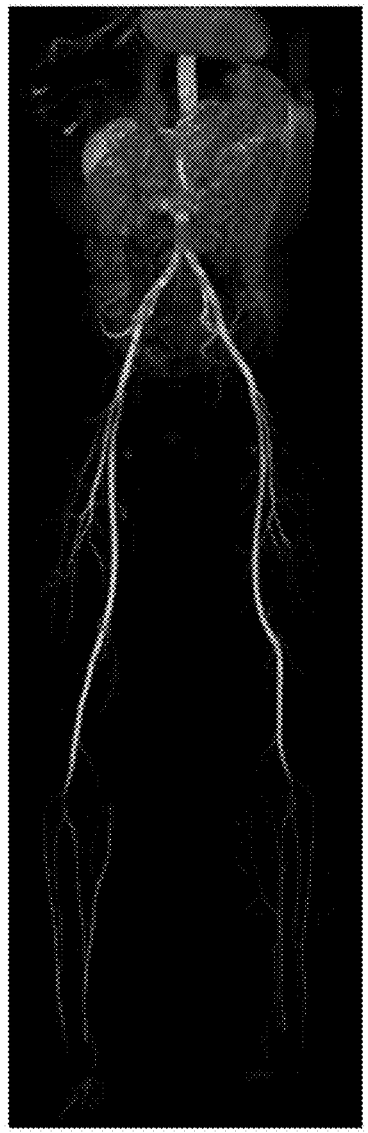
Figure 26D:

FIGS. 26A-26D illustrate four 2D coronal images of a region of interest depicting vasculature including a plurality of blood vessels. As shown in the figures, each 2D image was generated by combining three sub-images. FIG. 26A illustrates a 2D image that was generated without registration. FIG. 26B illustrates a 2D image of the same region of interest that was generated based solely on 3D registration. FIG. 26C and FIG. 26D are 2D images of the same region of interest from different view angles. The images were generated based on 2D registration and 3D registration utilizing the system and process according to some embodiments of the present disclosure.

Figure 27A:
FIGS. 27A and 27B illustrate coronal images of different view angles that are composed according to some embodiments of the present disclosure.
Figure 27B:
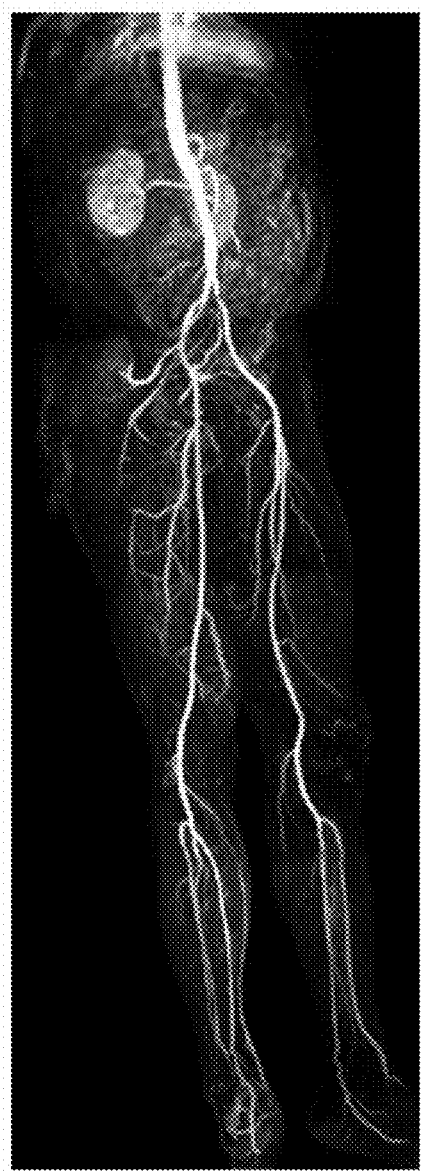

FIG. 27A and FIG. 27B are 2D coronal images of a same region of interest from different view angles. The images were generated based on 2D registration and 3D registration utilizing the system and process according to some embodiments of the present disclosure.

Figure 28A:
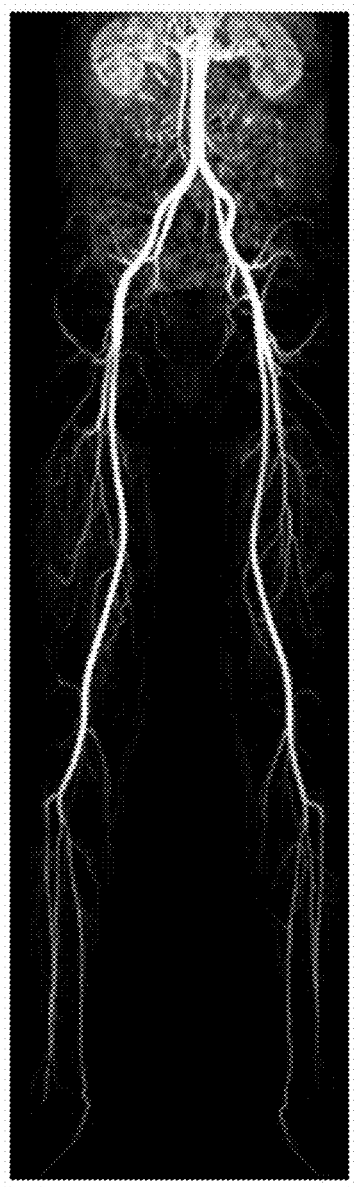
FIGS. 28A and 28B illustrate coronal images of different view angles that are composed according to some embodiments of the present disclosure.
Figure 28B:
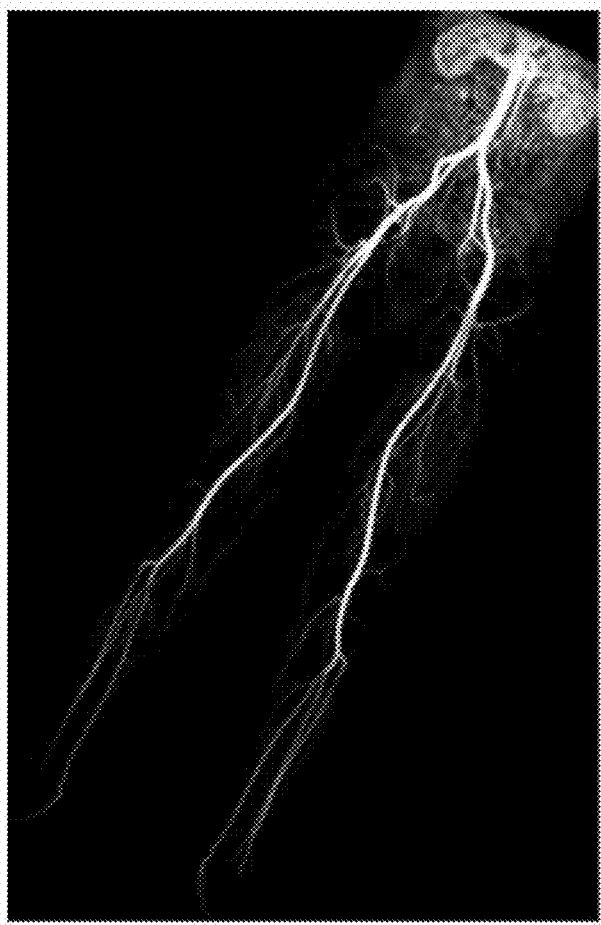

FIG. 28A and FIG. 28B are 2D coronal images of a same region of interest from different view angles that were generated based on 2D and 3D registration by utilizing the system and process according to some embodiments of the present disclosure.

Figure 29A:
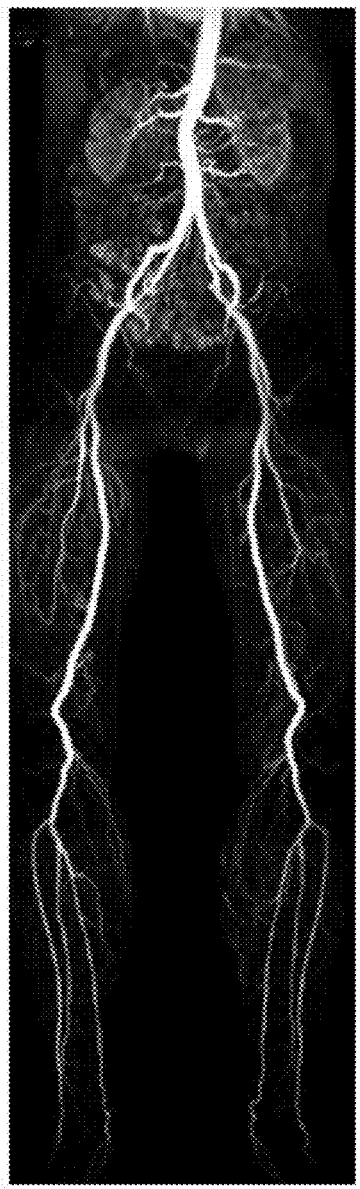
FIGS. 29A and 29B illustrate coronal images of different view angles that are composed according to some embodiments of the present disclosure.
Figure 29B:
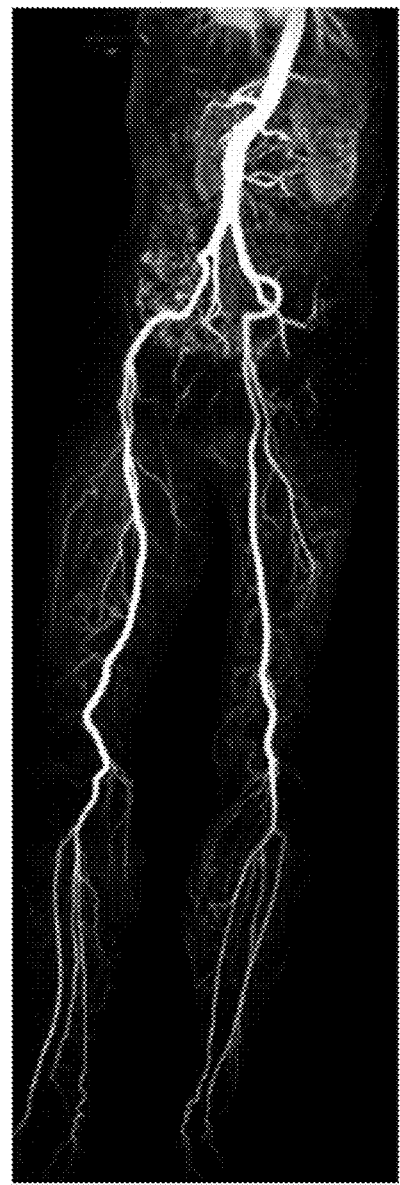

FIG. 29A and FIG. 29B are 2D coronal images of different view angles that were generated based on 2D and 3D registration by utilizing the system and process according to some embodiments of the present disclosure.

It should be noted that the above description of the embodiments are provided for the purposes of comprehending the present disclosure, and not intended to limit the scope of the present disclosure. For persons having ordinary skills in the art, various variations and modifications may be conducted in the light of the present disclosure. However, those variations and the modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

We claim:

1. An image composition system comprising:
   an acquisition engine configured to retrieve a first sub-image and a second sub-image; the first sub-image corresponding to a first set of 3D volume data, and the second sub-image corresponding to a second set of 3D volume data;
   an image processing engine configured to perform operations comprising
      retrieving a first overlapping image from the first sub-image;
      retrieving a second overlapping image from the second sub-image;
      generating a first 2D projection image and a first pixel map based on maximum intensity projection of the first overlapping image onto a plane;
      generating a second 2D projection image and a second pixel map based on maximum intensity projection of the second overlapping image onto the plane;
      performing 2D registration based on the first 2D projection image, the first pixel map, the second 2D projection image, and the second pixel map;
      performing 3D registration based on the 2D registration, the first pixel map, or the second pixel map;
      identifying a correlation between of the first sub-image including the first overlapping image and the second sub-image including the second overlapping image based on the 2D registration or the 3D registration; and
      fusing the first overlapping image and the second overlapping image based on the correlation to provide a composite image.

2. The image composition system of claim 1, the first sub-image or the second sub-image comprising a coronal image, a sagittal image, or a transverse image.

3. The image composition system of claim 1, the plane comprising a coronal plane, a sagittal plane, or a transverse plane.

4. The image composition system of claim 1, retrieving the first sub-image or retrieving the second sub-image comprising using DSA (digital subtraction angiography), CT (computed tomography), CTA (computed tomography angiography), PET (positron emission tomography), X-ray, MM (magnetic resonance imaging), MRA (magnetic resonance angiography), SPECT (single-photon emission computerized tomography), or US (ultrasound scanning).

5. The image composition system of claim 1, retrieving the first overlapping image or retrieving the second overlapping image comprising using Digital Imaging and Communication in Medicine.

6. The image composition system of claim 1, performing 2D registration comprising calculating an offset in a direction within the plane, and
   the offset comprising an X offset, a Y offset, a Z offset, a coronal offset, a sagittal offset, or a transverse offset.

7. The image composition system of claim 1, the performing 3D registration comprising calculating an offset in a direction perpendicular to the plane, and
   the offset comprising an X offset, a Y offset, a Z offset, a coronal, a sagittal offset, or a transverse offset.

8. The image composition system of claim 1 further comprising
   performing a fine registration based on recursion, a bisection method, an exhaustive method, a greedy algorithm, a divide and conquer algorithm, dynamic programming method, an iterative method, a branch-and-bound algorithm, or a backtracking algorithm.

9. The image composition system of claim 1,
   the first pixel map comprising information identifying first locations of maximum intensity of the first overlapping image, the first locations being in a direction perpendicular to the plane; and
   the second pixel map comprising information identifying second locations of maximum intensity of the second overlapping image, the second locations being in a direction perpendicular to the plane.

10. The image composition system of claim 9, the performing 3D registration comprising
    calculating a plurality of differences between the first locations and the second locations, each one of the plurality of differences corresponding to a pixel within the plane;
    comparing the plurality of differences to obtain a probability of the differences; and
    designating an offset in the direction perpendicular to the plane based on the probability.

11. The image composition system of claim 10, the second pixel map comprising a calibrated pixel map based on the 2D registration.

* * * * *